US012059525B2

(12) United States Patent
Jones et al.

(10) Patent No.: US 12,059,525 B2
(45) Date of Patent: Aug. 13, 2024

(54) SUBSTITUTE SMOKING DEVICE COMPRISING MULTIPLE AEROSOLS AND PASSIVE AEROSOL GENERATION

(71) Applicant: NERUDIA LIMITED, Speke (GB)

(72) Inventors: David Jones, Liverpool (GB); Chris Lord, Liverpool (GB); Tom Sudlow, Liverpool (GB); Edward Ross Shenton, Liverpool (GB); Andrew Austin, Liverpool (GB); Tamas Sajtos, Liverpool (GB)

( * ) Notice: Subject to any disclaimer, the term of this patent is extended or adjusted under 35 U.S.C. 154(b) by 1014 days.

(21) Appl. No.: 17/002,248

(22) Filed: Aug. 25, 2020

(65) Prior Publication Data

US 2021/0068455 A1     Mar. 11, 2021

Related U.S. Application Data

(63) Continuation of application No. PCT/EP2019/054292, filed on Feb. 21, 2019, and a
(Continued)

(30) Foreign Application Priority Data

Feb. 26, 2018 (GB) ........................................ 1803101
Feb. 26, 2018 (GB) ........................................ 1803104
(Continued)

(51) Int. Cl.
*A61M 15/06*       (2006.01)
*A24F 40/30*       (2020.01)
(Continued)

(52) U.S. Cl.
CPC ............ *A61M 15/06* (2013.01); *A24F 40/30* (2020.01); *A24F 40/48* (2020.01); *A24F 40/485* (2020.01);
(Continued)

(58) Field of Classification Search
None
See application file for complete search history.

(56) References Cited

U.S. PATENT DOCUMENTS

| 3,014,844 A | 12/1961 | Thiel et al. |
| 4,184,496 A | 1/1980 | Adair |

(Continued)

FOREIGN PATENT DOCUMENTS

| CN | 203168036 U | 9/2013 |
| CN | 106235420 A | 12/2016 |

(Continued)

OTHER PUBLICATIONS

EPO, International Search Report and Written Opinion, Application No. PCT/EP19/54288, dated Jun. 3, 2019.
(Continued)

*Primary Examiner* — Tho D Ta
(74) *Attorney, Agent, or Firm* — Perkins Coie LLP; Kenneth H. Ohriner

(57) ABSTRACT

There is disclosed an aerosol delivery device. The aerosol delivery device includes a first aerosol first aerosol sized for pulmonary penetration; and a second aerosol sized to inhibit pulmonary penetration. The second aerosol is transmissible within at least one of: a mammalian oral cavity and a mammalian nasal cavity, and the second aerosol comprising an active component for activating at least one of: one or more taste receptors in said oral cavity and one or more olfactory receptors in said nasal cavity. The second aerosol generator includes a Venturi aperture to generate the second aerosol.

There is disclosed a consumable for a substitute smoking device and a substitute smoking system. The consumable includes an airflow passage between an upstream inlet of the
(Continued)

consumable and a downstream outlet of the consumable. The consumable also includes a porous member for passive aerosol generation. The airflow passage is constricted by the porous member to form a narrowed portion of the airflow passage.

In another embodiment, the consumable also includes an inner porous member (315) for passive aerosol generation. The airflow passage has an annular portion surrounding at least a portion of the porous member.

In another embodiment, a portion of the airflow passage is located between a porous surface of the porous member and an opposing airflow passage wall. A minimum distance between the porous surface of the porous member and the opposing airflow passage wall is less than 1000 microns.

In another embodiment, the consumable also includes a porous member (315) for passive aerosol generation located within the airflow passage. The porous member is tapered along a longitudinal axis of the consumable.

In another embodiment, the consumable has a longitudinal axis and includes an airflow passage (308) between an upstream inlet of the consumable and a downstream outlet of the consumable. The consumable also includes a porous member (315) for passive aerosol generation. A longitudinal cross section of the airflow passage includes an inclined portion forming a passage angle with the longitudinal axis of the consumable. The passage angle is greater than zero degrees and less than 90 degrees and a wall of the inclined portion is formed from a porous surface (318) of the porous member.

In another embodiment, the consumable includes an active aerosol generator (304) for generating a first aerosol from a first aerosol precursor (310), and a passive aerosol generator (305) for generating a second aerosol from a second aerosol precursor (316).

In another embodiment, the consumable also includes an aerosol generator for generating an aerosol. An external portion of the aerosol generator is located at the outlet of the consumable.

In another embodiment, the consumable also includes an aerosol generator for generating an aerosol at an aerosol generation location. The aerosol generation location is substantially at the outlet located at a mouthpiece of the consumable.

In another embodiment, the outlet is located at a mouthpiece portion of the consumable; and the mouthpiece portion includes a nozzle for control of an aerosol from the aerosol generator.

20 Claims, 23 Drawing Sheets

Related U.S. Application Data continuation of application No. PCT/EP2019/054290, filed on Feb. 21, 2019, and a continuation of application No. PCT/EP2019/054307, filed on Feb. 21, 2019, and a continuation of application No. PCT/EP2019/054298, filed on Feb. 21, 2019, and a continuation of application No. PCT/EP2019/054288, filed on Feb. 21, 2019, and a continuation of application No. PCT/EP2019/054309, filed on Feb. 21, 2019, and a continuation of application No. PCT/EP2019/054311, filed on Feb. 21, 2019, and a continuation of application No. PCT/EP2019/054304, filed on Feb. 21, 2019, and a continuation of application No. PCT/EP2019/054291, filed on Feb. 21, 2019, and a continuation of application No. PCT/EP2019/054297, filed on Feb. 21, 2019.

(30) Foreign Application Priority Data

| Feb. 26, 2018 | (GB) | ..................................... | 1803106 |
|---|---|---|---|
| Feb. 26, 2018 | (GB) | ..................................... | 1803107 |
| Feb. 26, 2018 | (GB) | ..................................... | 1803110 |
| Feb. 26, 2018 | (GB) | ..................................... | 1803111 |
| Feb. 26, 2018 | (GB) | ..................................... | 1803113 |
| Feb. 26, 2018 | (GB) | ..................................... | 1803116 |
| Feb. 26, 2018 | (GB) | ..................................... | 1803120 |
| Feb. 26, 2018 | (GB) | ..................................... | 1803122 |

(51) Int. Cl.
  *A24F 40/48* (2020.01)
  *A24F 40/485* (2020.01)
  *A61M 11/04* (2006.01)
  *A24F 40/10* (2020.01)
  *A61M 15/00* (2006.01)

(52) U.S. Cl.
  CPC ............ *A61M 11/042* (2014.02); *A24F 40/10* (2020.01); *A61M 15/0085* (2013.01); *A61M 2205/0294* (2013.01); *A61M 2205/8206* (2013.01); *A61M 2206/14* (2013.01); *H05B 2203/021* (2013.01)

(56) References Cited

U.S. PATENT DOCUMENTS

| 4,284,089 | A | 8/1981 | Ray |
|---|---|---|---|
| 4,765,347 | A | 8/1988 | Sensabaugh, Jr. et al. |
| 4,774,971 | A | 10/1988 | Vieten |
| 4,945,929 | A | 8/1990 | Egilmex |
| 5,101,838 | A | 4/1992 | Schwartz |
| 5,137,034 | A | 8/1992 | Perfetti et al. |
| 6,216,705 | B1 | 4/2001 | Ossepian |
| 6,234,167 | B1 | 5/2001 | Cox |
| 9,888,719 | B2 | 2/2018 | Cadieux |
| 10,368,581 | B2 | 8/2019 | Rostami et al. |
| 10,426,197 | B2 | 10/2019 | Thorens |
| 10,645,970 | B2 | 5/2020 | Borkovec et al. |
| 10,932,492 | B2 | 3/2021 | Zinovik |
| 10,952,471 | B2 | 3/2021 | Batista et al. |
| 11,090,450 | B2 | 8/2021 | Li et al. |
| 11,116,919 | B2 | 9/2021 | Buchberger |
| 11,559,085 | B2 | 1/2023 | Fujinaga |
| 11,633,556 | B2 | 4/2023 | Jones et al. |
| 2002/0170566 | A1 | 11/2002 | Farr |
| 2002/0179102 | A1 | 12/2002 | Farr |
| 2003/0234297 | A1 | 12/2003 | Bloom |
| 2006/0207596 | A1 | 9/2006 | Lane |
| 2007/0248548 | A1 | 10/2007 | Blondino et al. |
| 2007/0267032 | A1 | 11/2007 | Shan |
| 2008/0092912 | A1 | 4/2008 | Robinson |
| 2010/0124535 | A1 | 5/2010 | Loxley et al. |
| 2011/0094523 | A1 | 4/2011 | Thorens |
| 2012/0111346 | A1 | 5/2012 | Rinker |
| 2012/0318882 | A1 | 12/2012 | Abehasera |
| 2013/0192615 | A1 | 8/2013 | Tucker |
| 2014/0209105 | A1 | 7/2014 | Sears |
| 2014/0261488 | A1 | 9/2014 | Tucker |
| 2014/0332014 | A1 | 11/2014 | Penrose |
| 2015/0122276 | A1 | 5/2015 | Johnson |
| 2015/0257447 | A1 | 9/2015 | Sullivan |
| 2015/0283070 | A1 | 10/2015 | Stenzler et al. |
| 2015/0374938 | A1 | 12/2015 | Scheiber |
| 2016/0044966 | A1 | 2/2016 | Li et al. |
| 2016/0058959 | A1 | 3/2016 | Hearn |
| 2016/0081394 | A1 | 3/2016 | Alarcon |
| 2016/0089508 | A1 | 3/2016 | Smith |

(56) References Cited

U.S. PATENT DOCUMENTS

| | | | |
|---|---|---|---|
| 2016/0106936 A1* | 4/2016 | Kimmel | A24F 40/485 |
| | | | 392/404 |
| 2016/0135506 A1 | 5/2016 | Sanchez | |
| 2016/0213065 A1 | 7/2016 | Wensley | |
| 2016/0213866 A1 | 7/2016 | Tan | |
| 2016/0228658 A1 | 8/2016 | Minskoff | |
| 2016/0262456 A1 | 9/2016 | Borkovec et al. | |
| 2016/0262457 A1* | 9/2016 | Borkovec | A61M 15/002 |
| 2016/0324216 A1 | 11/2016 | Li | |
| 2016/0330999 A1 | 11/2016 | Cameron | |
| 2017/0071249 A1 | 3/2017 | Ampolini et al. | |
| 2017/0157341 A1 | 6/2017 | Pandya et al. | |
| 2017/0251722 A1 | 9/2017 | Kobal | |
| 2017/0251723 A1 | 9/2017 | Kobal | |
| 2017/0304563 A1* | 10/2017 | Adelson | A61M 15/003 |
| 2017/0354184 A1 | 12/2017 | Mironov | |
| 2017/0360093 A1 | 12/2017 | Fernando | |
| 2018/0007966 A1 | 1/2018 | Li | |
| 2018/0007967 A1* | 1/2018 | Davis | A24F 40/05 |
| 2018/0027875 A1 | 2/2018 | Rostami et al. | |
| 2018/0027882 A1 | 2/2018 | Hepworth | |
| 2018/0029782 A1* | 2/2018 | Zuber | B05B 9/0822 |
| 2018/0170566 A1 | 6/2018 | Paolini et al. | |
| 2018/0304283 A1 | 10/2018 | Kazuaki | |
| 2020/0230333 A1 | 7/2020 | Jones et al. | |
| 2021/0235769 A1 | 8/2021 | Marubashi | |
| 2022/0287361 A1 | 9/2022 | Kim | |
| 2023/0030615 A1 | 2/2023 | Jang | |
| 2023/0292839 A1 | 9/2023 | Kim | |

FOREIGN PATENT DOCUMENTS

| | | |
|---|---|---|
| CN | 205987968 U | 3/2017 |
| EP | 295122 A2 | 12/1988 |
| EP | 3097803 A1 | 11/2016 |
| EP | 3135136 A1 | 3/2017 |
| EP | 3135138 A1 | 3/2017 |
| EP | 3158883 A2 | 4/2017 |
| GB | 2032244 A | 5/1980 |
| GB | 2115676 A | 9/1983 |
| GB | 2529727 A | 3/2016 |
| GB | 2536306 | 9/2016 |
| GB | 2536307 | 9/2016 |
| GB | 2542404 A | 3/2017 |
| GB | 2553136 A | 2/2018 |
| GB | 2556331 A | 5/2018 |
| JP | 1990-171174 A | 7/1990 |
| JP | 2007-511437 A | 5/2007 |
| JP | 2015-506182 A | 3/2015 |
| JP | 2016-215134 A | 12/2016 |
| KR | 20-2014-0002296 U | 4/2014 |
| RU | 2446895 | 4/2012 |
| RU | 2551311 | 5/2015 |
| RU | 2613785 | 3/2017 |
| RU | 2015146869 | 6/2017 |
| WO | 2005049449 A1 | 6/2005 |
| WO | 2013000967 A1 | 1/2013 |
| WO | 2013083638 A1 | 6/2013 |
| WO | WO2013133903 | 9/2013 |
| WO | 2013178769 A1 | 12/2013 |
| WO | 2014012907 | 1/2014 |
| WO | 2014150131 A1 | 9/2014 |
| WO | WO2014140273 | 9/2014 |
| WO | 2015013109 A1 | 1/2015 |
| WO | 2015112750 A1 | 7/2015 |
| WO | 2015179388 A1 | 11/2015 |
| WO | 2016050244 A1 | 4/2016 |
| WO | 2016062777 A | 4/2016 |
| WO | WO2016050245 A1 | 4/2016 |
| WO | 2016096497 A1 | 6/2016 |
| WO | 2016124740 A1 | 8/2016 |
| WO | 2016135331 A1 | 9/2016 |
| WO | 2016135342 A2 | 9/2016 |
| WO | WO2017015303 | 1/2017 |
| WO | WO2017032695 | 3/2017 |
| WO | 2017068101 A1 | 4/2017 |
| WO | 2017093357 A1 | 6/2017 |
| WO | 2017149152 | 9/2017 |
| WO | 2017149534 | 9/2017 |
| WO | 2017180151 A1 | 10/2017 |
| WO | 2017185051 A1 | 10/2017 |
| WO | 2017202953 | 11/2017 |
| WO | 2018007633 | 1/2018 |
| WO | 2018050720 A1 | 3/2018 |
| WO | 2018083037 A1 | 5/2018 |
| WO | 2019057857 A1 | 3/2019 |

OTHER PUBLICATIONS

EPO, International Search Report and Written Opinion, Application No. PCT/EP19/54290, dated Jun. 4, 2019.
EPO, International Search Report and Written Opinion, Application No. PCT/EP19/54291, dated Jun. 6, 2019.
EPO, International Search Report and Written Opinion, Application No. PCT/EP19/54292, dated Jun. 4, 2019.
EPO, International Search Report and Written Opinion, Application No. PCT/EP19/54297, dated Jun. 6, 2019.
EPO, International Search Report and Written Opinion, Application No. PCT/EP19/54298, dated Jun. 6, 2019.
EPO, International Search Report and Written Opinion, Application No. PCT/EP19/54304, dated Jun. 5, 2019.
EPO, International Search Report and Written Opinion, Application No. PCT/EP19/54307, dated Jun. 4, 2019.
EPO, International Search Report and Written Opinion, Application No. PCT/EP19/54309, dated May 31, 2019.
EPO, International Search Report and Written Opinion, Application No. PCT/EP19/54311, dated Jun. 5, 2019.
IP Office UK, Combined Search and Examination Report, Application No. GB1803101.3, dated Aug. 7, 2018.
IP Office UK, Combined Search and Examination Report, Application No. GB1803104.7, dated May 23, 2018.
IP Office UK, Combined Search and Examination Report, Application No. GB1803106.2, dated Jun. 12, 2018.
IP Office UK, Combined Search and Examination Report, Application No. GB1803107.0, dated Jun. 15, 2018.
IP Office UK, Combined Search and Examination Report, Application No. GB1803110.4, dated Jul. 5, 2018.
IP Office UK, Combined Search and Examination Report, Application No. GB1803111.2, dated Aug. 1, 2018.
IP Office UK, Combined Search and Examination Report, Application No. GB1803113.8, dated Aug. 17, 2018.
IP Office UK, Combined Search and Examination Report, Application No. GB1803116.1, dated Aug. 20, 2018.
IP Office UK, Combined Search and Examination Report, Application No. GB1803120.3, dated Jun. 29, 2018.
IP Office UK, Combined Search and Examination Report, Application No. GB1803122.9, dated Aug. 10, 2018.
USPTO, Nonfinal Office Action for U.S. Appl. No. 18/191,820, dated Nov. 14, 2023.
Eslamian, M. et al., Handbook of Atomization and Sprays, Chapter 33—"Swirl, T-Jet and Vibrating-Mesh Atomizers"; Springer Science + Business Media, LLC, 2011, 755-773.
Fernandez Tena, Ana et al.; "Deposition of Inhaled Particles in the Lungs", Archovos De Bronconeumolgia, 2012; 48(7) 240-246.
Lozano, A. et al.; "High-Frequency Ultrasonic Atomisation with Pulsed Excitation"; Journal of Fluid Engineering, Nov. 2003, vol. 125, 941-945.
Sono-Tek Corporation; "Ultrasonic Atomisation Technology for Precise Coatings", at www.sono-tek.com/ultrasonic-nozzle-technology/ and downloaded May 23, 2017.
Vecellio L; "The mesh nebuliser: a recent technical innovation for aerosol delivery", Breathe, Mar. 2006, vol. 2, No. 3, pp. 253-260.
International Search Report and Written Opinion of International Application No. PCT/EP2018/075697; dated Dec. 7, 2018; 13 pages.
Combined Search and Examination Report for U.K. Appl. No. GB1715386.7; dated Mar. 22, 2018; 7 pages.

(56) References Cited

OTHER PUBLICATIONS

EPO, Exam Report for European Application No. 18779325.2, dated Oct. 31, 2022.
IP Office Japan, Reasons for Refusal of Japanese Application No. 2020-516899, dated May 27, 2022, English machine translation.
IP Office Japan, Reasons for Refusal of Japanese Application No. 2020-516899, dated Jan. 17, 2023, with English translation.
IP Office Japan, Reasons for Refusal of Japanese Application No. 2020-568031, dated Jan. 4, 2023, with English translation.
Ip Office Japan, Reasons for Refusal of Japanese Application No. 2020-568032, dated Jan. 17, 2023, with English translation.
IP Office Japan, Reasons for Refusal of Japanese Application No. 2020-568033, dated Jan. 17, 2023, with English translation.
IP Office Japan, Reasons for Refusal of Japanese Application No. 2020-568034, dated Jan. 17, 2023, with English translation.
USPTO, Nonfinal Office Action for U.S. Appl. No. 16/648,483, dated Mar. 14, 2022.

* cited by examiner

SUBSTITUTE SMOKING DEVICE COMPRISING MULTIPLE AEROSOLS AND PASSIVE AEROSOL GENERATION

This application is a continuation of International Patent Application Numbers:

PCT/EP2019/054288, filed Feb. 21, 2019, which claims the benefit of Great Britain Patent Application No. 1803122.9, filed Feb. 26, 2018;

PCT/EP2019/054290, filed Feb. 21, 2019, which claims the benefit of Great Britain Patent Application No. 1803120.3, filed Feb. 26, 2018;

PCT/EP2019/054291, filed Feb. 21, 2019, which claims the benefit of Great Britain Patent Application No. 1803116.1, filed Feb. 26, 2018;

PCT/EP2019/054292, filed Feb. 21, 2019, which claims the benefit of Great Britain Patent Application No. 1803113.8, filed Feb. 26, 2018;

PCT/EP2019/054297, filed Feb. 21, 2019, which claims the benefit of Great Britain Patent Application No. 1803111.2, filed Feb. 26, 2018;

PCT/EP2019/054298, filed Feb. 21, 2019, which claims the benefit of Great Britain Patent Application No. 1803110.4, filed Feb. 26, 2018;

PCT/EP2019/054304, filed Feb. 21, 2019, which claims the benefit of Great Britain Patent Application No. 1803107.0, filed Feb. 26, 2018;

PCT/EP2019/054307, filed Feb. 21, 2019, which claims the benefit of Great Britain Patent Application No. 1803106.2, filed Feb. 26, 2018;

PCT/EP2019/054309, filed Feb. 21, 2019, which claims the benefit of Great Britain Patent Application No. 1803104.7, filed Feb. 26, 2018; and PCT/EP2019/054311, filed Feb. 21, 2019, which claims the benefit of Great Britain Patent Application No. 1803101.3, filed Feb. 26, 2018;

all of which are incorporated herein by reference.

TECHNICAL FIELD

The present invention relates to a device, system and method for the delivery of aerosols. In particular, but not exclusively, one or more embodiments in accordance with the present invention relate to the delivery of aerosols comprising different active components.

BACKGROUND

Nicotine replacement therapies are aimed at people who wish to stop smoking and overcome their dependence on nicotine. One form of nicotine replacement therapy is an inhaler or inhalator. These generally have the appearance of a plastic cigarette and are used by people who crave the behaviour associated with consumption of combustible tobacco—the so-called hand-to-mouth aspect—of smoking tobacco. An inhalator comprises a replaceable nicotine cartridge. When a user inhales through the device, nicotine is atomised or aerosolised from the cartridge and is absorbed through the mucous membranes in the mouth and throat, rather than travelling into the lungs. Nicotine replacement therapies are generally classified as medicinal products and are regulated under the Human Medicines Regulations in the United Kingdom.

In addition to passive nicotine delivery devices such as the Inhalator, active nicotine delivery devices exist in the form of electronic cigarettes. The inhaled aerosol mist or vapour typically bears nicotine and/or flavourings. In use, the user may experience a similar satisfaction and physical sensation to those experienced from combustible tobacco products, and exhales an aerosol mist or vapour of similar appearance to the smoke exhaled when using such combustible tobacco products.

A smoking-substitute device generally uses heat and/or ultrasonic agitation to vapourise/aerosolise a solution comprising nicotine and/or other flavouring, propylene glycol and/or glycerol formulation into an aerosol, mist, or vapour for inhalation. A person of ordinary skill in the art will appreciate that the term "smoking-substitute device" as used herein includes, but is not limited to, electronic nicotine delivery systems (ENDS), electronic cigarettes, e-cigarettes, e-cigs, vaping cigarettes, pipes, cigars, cigarillos, vapourisers and devices of a similar nature that function to produce an aerosol mist or vapour that is inhaled by a user. Some electronic cigarettes are disposable; others are reusable, with replaceable and refillable parts.

Smoking-substitute devices may resemble a traditional cigarette and are cylindrical in form with a mouthpiece at one end through which the user can draw the aerosol, mist or vapour for inhalation. These devices usually share several common components; a power source such as a battery, a reservoir for holding the liquid to be vapourised (often termed an e-liquid), a vapourisation component such as a heater for atomizing, aerosolising and/or vapourising the liquid and to thereby produce an aerosol, mist or vapour, and control circuitry operable to actuate the vapourisation component responsive to an actuation signal from a switch operative by a user or configured to detect when the user draws air through the mouthpiece by inhaling.

The popularity and use of smoking-substitute devices has grown rapidly in the past few years.

Aspects and embodiments of the invention were devised with the foregoing in mind.

SUMMARY

According to a first aspect of the invention, there is provided an aerosol delivery device comprising: a first aerosol generator to generate a first aerosol from a first aerosol precursor and to introduce said first aerosol into a first fluid flow pathway, wherein said first aerosol is sized for pulmonary penetration; a second aerosol generator to generate a second aerosol from a second aerosol precursor and to introduce the second aerosol into a second fluid flow pathway, wherein the second aerosol is sized to inhibit pulmonary penetration; the second aerosol is transmissible within at least one of: a mammalian oral cavity and a mammalian nasal cavity, and the second aerosol comprising an active component for activating at least one of: one or more taste receptors in said oral cavity and one or more olfactory receptors in said nasal cavity, a Venturi aperture to dispense and aerosolise the second aerosol precursor in the second aerosol generator, wherein the second aerosol precursor is a liquid.

Advantageously, said second aerosol generator comprises a porous member for containing the second aerosol precursor.

Conveniently, the porous member includes a porous wicking material.

Preferably, a portion of the porous member is located in a low pressure region, wherein in use, the Venturi aperture forms the low pressure region.

Advantageously, in use, the second aerosol is generated from a porous surface of the porous member into an airflow through the Venturi aperture.

Conveniently, the porous surface is located in the low pressure region.

Preferably, the Venturi aperture is located proximate to an outlet at a mouthpiece outlet of the aerosol delivery device.

Advantageously, the Venturi aperture is located substantially at a mouthpiece outlet of the consumable.

Advantageously, the second aerosol is at least one of: sized to inhibit penetration to the trachea; sized to inhibit penetration to the larynx; sized to inhibit penetration to the laryngopharynx; and sized to inhibit penetration to the oropharynx.

Advantageously, the second aerosol has a mass median aerodynamic diameter that is greater than or equal to 15 microns, in particular greater than 30 microns, more particularly greater than 50 microns, yet more particularly greater than 60 microns, and even more particularly greater than 70 microns.

Advantageously, the second aerosol has a maximum mass median aerodynamic diameter that is less than 300 microns, in particular less than 200 microns, yet more particularly less than 100 microns.

Advantageously, said first aerosol precursor comprises components such that the first aerosol comprises a pulmonary deliverable active component.

Advantageously, the first aerosol has a mass median aerodynamic diameter less than or equal to 10 microns, preferably less than 8 microns, more preferably less than 5 microns, yet more preferably less than 1 micron.

Advantageously, said first aerosol generator is configured to heat said first aerosol precursor.

Advantageously, said first aerosol generator is configured to agitate said first aerosol precursor.

Advantageously, said first fluid flow pathway further receives said first aerosols from a first aerosol inlet of said device.

Advantageously, said first aerosol inlet is configured to inject said first aerosol into said first fluid flow pathway.

Advantageously, said second fluid flow pathway further receives said second aerosol from a second aerosol inlet of said device.

Advantageously, said second aerosol inlet is configured to inject said second aerosols into said second fluid flow pathway.

Advantageously, said first fluid pathway and said second fluid flow pathway merge together.

Advantageously, said first fluid pathway and said second fluid flow pathway are contiguous.

Advantageously, said second fluid flow pathway is disposed along a longitudinal axis of said first fluid flow pathway.

Advantageously, said first fluid flow pathway is disposed proximal to a gas inlet of said device and said second fluid flow pathway is disposed proximal to an aerosol outlet of said device.

Advantageously, said second fluid flow pathway is disposed proximal to a gas inlet of said device and said first fluid flow pathway is disposed proximal to an aerosol outlet of said device.

Advantageously, said second fluid flow pathway is disposed co-axially relative to said first fluid flow pathway.

Advantageously, said second fluid flow pathway is disposed adjacent said first fluid flow pathway in a side by side relationship therewith.

Advantageously, said first fluid flow pathway is separated from said second fluid flow pathway by a wall member.

Advantageously, said first fluid flow pathway comprising a first housing to constrain said fluid flow and said second fluid flow pathway comprising a second housing to constrain said second fluid flow, said first housing to receive said first aerosol; and said second housing to receive said second aerosol.

Advantageously, said first housing comprising said first aerosol generator and/or said second housing comprising said second aerosol generator.

Advantageously, said first housing comprises a removable module of said delivery device.

Advantageously, said first housing comprises a replaceable module of said delivery device.

Advantageously, said first housing comprises a refillable module of said delivery device.

Advantageously, said second housing comprises a removable module of said delivery device.

Advantageously, said second housing comprises a replaceable module of said delivery device.

Advantageously, said second housing comprises a refillable module of said delivery device.

Advantageously, said first aerosol precursor comprises nicotine, or a nicotine derivative, or a nicotine analogue.

Advantageously, said first aerosol precursor comprises a pulmonary deliverable active component that is a free nicotine salt comprising at least one of: nicotine hydrochloride; nicotine dihydrochloride; nicotine monotartrate; nicotine bitartrate; nicotine bitartrate dihydrate; nicotine sulphate; nicotine zinc chloride monohydrate; and nicotine salicylate.

Advantageously, said second aerosol being transmissible to activate at least one of: one or more taste receptors in said oral cavity; and one or more olfactory receptors in said nasal cavity.

Advantageously, said first aerosol generator is configured to generate the first aerosol from a first aerosol precursor comprising at least one of: glycol; polyglycol; and water.

Advantageously, said second aerosol generator is configured to introduce said second aerosol into said fluid flow pathway at a pre-set period of time following an actuation of said first aerosol generator.

Advantageously, said second fluid flow pathway comprises at least one baffle configured such that a portion of said second aerosol impinges on said baffle.

Advantageously, said aerosol inlet port is configured to introduce the second aerosol of a mass median aerodynamic diameter to inhibit pulmonary penetration.

Advantageously, said second aerosol generator comprises a piezoelectric element to dispense and aerosolise the second aerosol precursor in the second aerosol generator, wherein the second aerosol precursor is a liquid.

Advantageously, said second aerosol generator comprises a precursor substrate for the second aerosol precursor, wherein the precursor substrate comprises a hydrophobic surface.

Advantageously, said second aerosol generator comprises a plurality of capillary tubes configured to draw the second aerosol precursor from a reservoir of second aerosol precursor to a free end of the plurality of capillary tubes.

Advantageously, the free end of the plurality of capillary tubes is hydrophobic.

Advantageously, said first aerosol is of a size suitable for deep lung penetration.

Advantageously, said first aerosol has a mass median aerodynamic diameter less than 2 µm.

Advantageously, said second fluid flow pathway terminates in a second fluid flow pathway mouthpiece.

Advantageously, said first fluid flow pathway terminates in a first fluid flow pathway mouthpiece.

Advantageously, said first and second fluid flow pathways terminate in a combination mouthpiece.

Advantageously, said combination mouthpiece comprises separate pathways corresponding to said first and second fluid flow pathways respectively.

Advantageously, said merged first and second fluid flow pathways terminate in a mouthpiece.

Advantageously, said active component comprises a physiologically active component.

According to another aspect, a first fluid pathway housing is provided, the first fluid pathway housing being for an aerosol delivery device according to the first aspect.

Advantageously, the first fluid pathway housing comprises said first aerosol precursor.

Advantageously, the first fluid pathway housing comprises said first aerosol generator.

According to a further aspect of the invention, a second fluid pathway housing is provided, the second fluid pathway housing being for an aerosol delivery device according to the first aspect.

Advantageously, the second fluid pathway housing comprises said second aerosol precursor.

Advantageously, the second fluid pathway housing comprises said second aerosol generator.

According to a further aspect of the invention, a kit of parts is provided, the kits of parts being for an aerosol delivery device according to an above aspect, the kit of parts including a first fluid pathway housing according to an above aspect and a second fluid flow pathway housing according to an above aspect.

According to a further aspect of the invention, a consumable for a substitute smoking device is provided, the consumable including: an airflow passage between an upstream inlet of the consumable and a downstream outlet of the consumable; a porous member for passive aerosol generation; wherein, the airflow passage is constricted by the porous member to form a narrowed portion of the airflow passage.

Advantageously, a wall of the narrowed portion is formed from a porous surface of the porous member, such that, in use, an airflow along the narrowed portion passes across a porous surface of the porous member.

Preferably, an inner wall of the narrowed portion is formed from the porous surface of the porous member.

Conveniently, the porous member is located within the airflow passage.

Advantageously, an outer wall of the narrowed portion is formed from the porous surface of the porous member.

Preferably, the porous member is an inner porous member located within the narrowed portion, and the consumable further including an outer porous member radially outward of the narrowed portion.

Conveniently, the outer porous member substantially surrounds the narrowed portion.

Advantageously, the consumable is a flavour pod.

Preferably, the consumable further including an active aerosol generator for generating a first aerosol.

Conveniently, the first aerosol is sized for pulmonary penetration and the aerosol from the porous member is sized to inhibit pulmonary penetration.

Advantageously, the aerosol from the porous member is transmissible within at least one of: a mammalian oral cavity and a mammalian nasal cavity, and the aerosol from the porous member comprising an active component for activating at least one of: one or more taste receptors in said oral cavity and one or more olfactory receptors in said nasal cavity.

Preferably, the aerosol from the porous member is at least one of: sized to inhibit penetration to the trachea; sized to inhibit penetration to the larynx; sized to inhibit penetration to the laryngopharynx; and sized to inhibit penetration to the oropharynx.

Conveniently, the aerosol from the porous member has a mass median aerodynamic diameter that is greater than or equal to 15 microns, in particular greater than 30 microns, more particularly greater than 50 microns, yet more particularly greater than 60 microns, and even more particularly greater than 70 microns.

Advantageously, the aerosol from the porous member has a maximum mass median aerodynamic diameter that is less than 300 microns, in particular less than 200 microns, yet more particularly less than 100 microns.

Preferably, said first aerosol comprises a pulmonary deliverable active component.

Conveniently, the first aerosol has a mass median aerodynamic diameter less than or equal to 10 microns, preferably less than 8 microns, more preferably less than 5 microns, yet more preferably less than 1 micron.

Advantageously, the consumable is a cartomiser.

According to a further aspect of the invention, a substitute smoking system is provided, the system including: an airflow passage between an upstream inlet of a component of the system and a downstream outlet of the component; a porous member for passive aerosol generation; wherein, the airflow passage is constricted by the porous member to from a narrowed portion of the airflow passage.

According to a further aspect of the invention, a consumable for a substitute smoking device is provided, the consumable including: an airflow passage between an upstream inlet of the consumable and a downstream outlet of the consumable, and; an inner porous member for passive aerosol generation; wherein the airflow passage has an annular portion surrounding at least a portion of the porous member.

Preferably, an inner wall of the annular portion is formed by a porous surface of the porous member.

Conveniently, the annular portion has a transverse cross-sectional shape, wherein the transverse cross-sectional shape is one of circular, oval, rectangular, or triangular.

Advantageously, a distance between the porous member and an opposing wall is substantially constant around a circumferential surface of the porous member.

Preferably, the consumable is a flavour pod.

Conveniently, the consumable further including an active aerosol generator for generating a first aerosol.

Advantageously, the first aerosol is sized for pulmonary penetration and the aerosol from the porous member is sized to inhibit pulmonary penetration.

Preferably, the aerosol from the porous member is transmissible within at least one of: a mammalian oral cavity and a mammalian nasal cavity, and the aerosol from the porous member comprising an active component for activating at least one of: one or more taste receptors in said oral cavity and one or more olfactory receptors in said nasal cavity.

Conveniently, the aerosol from the porous member is at least one of: sized to inhibit penetration to the trachea; sized to inhibit penetration to the larynx; sized to inhibit penetration to the laryngopharynx; and sized to inhibit penetration to the oropharynx.

Advantageously, the aerosol from the porous member has a mass median aerodynamic diameter that is greater than or equal to 15 microns, in particular greater than 30 microns, more particularly greater than 50 microns, yet more particularly greater than 60 microns, and even more particularly greater than 70 microns.

Preferably, the aerosol from the porous member has a maximum mass median aerodynamic diameter that is less than 300 microns, in particular less than 200 microns, yet more particularly less than 100 microns.

Conveniently, said first aerosol comprises a pulmonary deliverable active component.

Advantageously, the first aerosol has a mass median aerodynamic diameter less than or equal to 10 microns, preferably less than 8 microns, more preferably less than 5 microns, yet more preferably less than 1 micron.

Preferably, the consumable is a cartomiser.

According to a further aspect of the invention, a substitute smoking system is provided, including: an airflow passage between an upstream inlet of a component of the substitute smoking system and a downstream outlet of the component, and; an inner porous member for passive aerosol generation; wherein the airflow passage has an annular portion surrounding at least a portion of the porous member.

According to a further aspect of the invention, a consumable for a substitute smoking device is provided, the consumable including: an airflow passage between an upstream inlet of the consumable and a downstream outlet of the consumable; a porous member for passive aerosol generation; wherein at least a portion of the airflow passage is located between a porous surface of the porous member and an opposing airflow passage wall; and wherein a minimum distance between the porous surface of the porous member and the opposing airflow passage wall is substantially less than 1000 microns.

Conveniently, the opposing airflow passage wall is formed from a non-porous material.

Advantageously, the opposing airflow passage wall is formed from a housing of the consumable.

Preferably, in longitudinal cross section, the opposing airflow passage wall is pointed towards the porous surface.

Conveniently, the porous member is an inner porous member, and wherein the opposing airflow passage wall is formed from a surface of an outer porous member.

Advantageously, the minimum distance between the porous surface of the porous member and the opposing airflow passage wall is substantially constant around a circumferential surface of the porous member.

Preferably, in longitudinal cross section, the opposing airflow passage wall includes a substantially flat portion.

Conveniently, in longitudinal cross section, the opposing airflow passage wall includes a curved portion.

Advantageously, in longitudinal cross section, the porous surface includes a substantially flat portion.

Preferably, in longitudinal cross section, the porous surface includes a curved portion.

Conveniently, the direction of curvature of the porous surface is opposite to the direction of curvature of the opposing airflow passage wall.

Advantageously, the consumable is a flavour pod.

Preferably, the consumable further including an active aerosol generator for generating a first aerosol.

Conveniently, the first aerosol is sized for pulmonary penetration and the aerosol from the porous member is sized to inhibit pulmonary penetration.

Advantageously, the aerosol from the porous member is transmissible within at least one of: a mammalian oral cavity and a mammalian nasal cavity, and the aerosol from the porous member comprising an active component for activating at least one of: one or more taste receptors in said oral cavity and one or more olfactory receptors in said nasal cavity.

Preferably, the aerosol from the porous member is at least one of: sized to inhibit penetration to the trachea; sized to inhibit penetration to the larynx; sized to inhibit penetration to the laryngopharynx; and sized to inhibit penetration to the oropharynx.

Conveniently, the aerosol from the porous member has a mass median aerodynamic diameter that is greater than or equal to 15 microns, in particular greater than 30 microns, more particularly greater than 50 microns, yet more particularly greater than 60 microns, and even more particularly greater than 70 microns.

Advantageously, the aerosol from the porous member has a maximum mass median aerodynamic diameter that is less than 300 microns, in particular less than 200 microns, yet more particularly less than 100 microns.

Preferably, said first aerosol comprises a pulmonary deliverable active component.

Conveniently, the first aerosol has a mass median aerodynamic diameter less than or equal to 10 microns, preferably less than 8 microns, more preferably less than 5 microns, yet more preferably less than 1 micron.

Advantageously, the consumable is a cartomiser.

According to a further aspect of the invention, a substitute smoking system is provided, including: an airflow passage between an upstream inlet of a component of the substitute smoking system and a downstream outlet of the component; a porous member for passive aerosol generation; wherein at least a portion of the airflow passage is located between a porous surface of the porous member and an opposing airflow passage wall; and wherein a minimum distance between the porous surface of the porous member and the opposing airflow passage wall is substantially less than 1000 micrometres.

According to a further aspect of the invention, a consumable for a substitute smoking device, the consumable including: an airflow passage between an upstream inlet of the consumable and a downstream outlet of the consumable, and; a porous member for passive aerosol generation located within the airflow passage; wherein the porous member is tapered along a longitudinal axis of the consumable.

Conveniently, the airflow passage surrounds the porous member.

Conveniently, the airflow passage comprises an annular portion surrounding the porous member.

Preferably, an opposing wall of the airflow passage is tapered along a longitudinal axis of the consumable in a region adjacent to the porous member.

Conveniently, the opposing wall and a porous surface of the porous member are substantially parallel along at least a parallel portion of the porous member.

Advantageously, the opposing wall and a porous surface of the porous member are substantially nonparallel along at least a non-parallel portion of the porous member.

Preferably, the porous member is tapered to form a rounded downstream tip.

Conveniently, the porous member is tapered to form a pointed downstream tip.

Advantageously, the porous member is tapered to form a flat downstream tip.

Preferably, the porous member is tapered to have a conical downstream portion.

Conveniently, the consumable is a flavour pod.

Advantageously, the consumable further including an active aerosol generator for generating a first aerosol.

Preferably, the first aerosol is sized for pulmonary penetration and the aerosol from the porous member is sized to inhibit pulmonary penetration.

Conveniently, the aerosol from the porous member is transmissible within at least one of: a mammalian oral cavity and a mammalian nasal cavity, and the aerosol from the porous member comprising an active component for activating at least one of: one or more taste receptors in said oral cavity and one or more olfactory receptors in said nasal cavity.

Advantageously, the aerosol from the porous member is at least one of: sized to inhibit penetration to the trachea; sized to inhibit penetration to the larynx; sized to inhibit penetration to the laryngopharynx; and sized to inhibit penetration to the oropharynx.

Preferably, the aerosol from the porous member has a mass median aerodynamic diameter that is greater than or equal to 15 microns, in particular greater than 30 microns, more particularly greater than 50 microns, yet more particularly greater than 60 microns, and even more particularly greater than 70 microns.

Conveniently, the aerosol from the porous member has a maximum mass median aerodynamic diameter that is less than 300 microns, in particular less than 200 microns, yet more particularly less than 100 microns.

Advantageously, said first aerosol comprises a pulmonary deliverable active component.

Preferably, the first aerosol has a mass median aerodynamic diameter less than or equal to 10 microns, preferably less than 8 microns, more preferably less than 5 microns, yet more preferably less than 1 micron.

Conveniently, the consumable is a cartomiser.

According to a further aspect of the invention, a substitute smoking system is provided, including: an airflow passage between an upstream inlet of a component of the system and a downstream outlet of the component, and; a porous member for passive aerosol generation located within the airflow passage; wherein the porous member is tapered along a longitudinal axis of the component.

According to a further aspect of the invention, a consumable for a substitute smoking device is provided, the consumable having a longitudinal axis, the consumable including: an airflow passage between an upstream inlet of the consumable and a downstream outlet of the consumable, and; a porous member for passive aerosol generation; wherein a longitudinal cross section of the airflow passage includes an inclined portion forming a passage angle with the longitudinal axis of the consumable, the passage angle being greater than zero degrees and less than 90 degrees, and; wherein a wall of the inclined portion is formed from a porous surface of the porous member.

Advantageously, in use, an airflow along the inclined portion passes across the porous surface of the porous member.

Preferably, the angled portion has a length of between 0.1 mm and 4 mm.

Conveniently, the passage angle is between 10 and 80 degrees.

Advantageously, the passage angle is between 20 and 70 degrees.

Preferably, the passage angle is between 30 and 60 degrees.

Conveniently, the passage angle is between 40 and 50 degrees.

Advantageously, the consumable is a flavour pod.

Preferably, the consumable further including an active aerosol generator for generating a first aerosol.

Conveniently, the first aerosol is sized for pulmonary penetration and the aerosol from the porous member is sized to inhibit pulmonary penetration.

Advantageously, the aerosol from the porous member is transmissible within at least one of: a mammalian oral cavity and a mammalian nasal cavity, and the aerosol from the porous member comprising an active component for activating at least one of: one or more taste receptors in said oral cavity and one or more olfactory receptors in said nasal cavity.

Preferably, the aerosol from the porous member is at least one of: sized to inhibit penetration to the trachea; sized to inhibit penetration to the larynx; sized to inhibit penetration to the laryngopharynx; and sized to inhibit penetration to the oropharynx.

Conveniently, the aerosol from the porous member has a mass median aerodynamic diameter that is greater than or equal to 15 microns, in particular greater than 30 microns, more particularly greater than 50 microns, yet more particularly greater than 60 microns, and even more particularly greater than 70 microns.

Advantageously, the aerosol from the porous member has a maximum mass median aerodynamic diameter that is less than 300 microns, in particular less than 200 microns, yet more particularly less than 100 microns.

Preferably, said first aerosol comprises a pulmonary deliverable active component.

Conveniently, the first aerosol has a mass median aerodynamic diameter less than or equal to 10 microns, preferably less than 8 microns, more preferably less than 5 microns, yet more preferably less than 1 micron.

Advantageously, the consumable is a cartomiser.

According to a further aspect of the invention, a substitute smoking system is provided, including a component having a longitudinal axis, the component including: an airflow passage between an upstream inlet of the component and a downstream outlet of the component, and; a porous member for passive aerosol generation; wherein a longitudinal cross section of the airflow passage includes an inclined portion forming a passage angle with the longitudinal axis of the component, the passage angle being greater than zero degrees and less than 90 degrees, and; wherein a wall of the inclined portion is formed from a porous surface of the porous member.

According to a further aspect of the invention, a consumable for a substitute smoking device is provided, the consumable including: an active aerosol generator for generating a first aerosol from a first aerosol precursor, and; a passive aerosol generator for generating a second aerosol from a second aerosol precursor.

Preferably, the consumable including: an airflow passage between an upstream inlet of the consumable and a downstream outlet of the consumable.

Conveniently, the passive aerosol generator is located downstream of the active aerosol generator.

Advantageously, the active aerosol generator is configured to deliver the first aerosol to a downstream outlet of the consumable, and; the passive aerosol generator is configured to deliver the second aerosol to the downstream outlet of the consumable.

Preferably, the active and passive aerosol generators are configured to deliver the respective first and second aerosols to the downstream outlet of the consumable simultaneously.

Conveniently, the active aerosol generator includes a heating device configured for heating the first aerosol precursor to generate the first aerosol.

Advantageously, the passive aerosol generator includes a porous member.

Preferably, the second aerosol precursor is stored within the pores of the porous member.

Advantageously, the consumable comprises a second aerosol precursor storage fluidly connected to the porous member, wherein second aerosol precursor from the second aerosol precursor storage is drawn into the porous member in use.

Conveniently, the passive aerosol generator is configured generate the second aerosol when an airflow is directed over a porous surface of the porous member.

Advantageously, the passive aerosol generator is configured to be electrically isolated from an electrical power source in the substitute smoking device when the consumable is engaged with the substitute smoking device.

Preferably, the active aerosol generator is configured to be electrically connected to an electrical power source in the substitute smoking device when the consumable is engaged with the substitute smoking device.

Conveniently, the first aerosol is sized for pulmonary penetration and the second aerosol is sized to inhibit pulmonary penetration.

Advantageously, the second aerosol is transmissible within at least one of: a mammalian oral cavity and a mammalian nasal cavity, and the aerosol from the porous member comprising an active component for activating at least one of: one or more taste receptors in said oral cavity and one or more olfactory receptors in said nasal cavity.

Preferably, the second aerosol is at least one of: sized to inhibit penetration to the trachea; sized to inhibit penetration to the larynx; sized to inhibit penetration to the laryngopharynx; and sized to inhibit penetration to the oropharynx.

Conveniently, the second aerosol has a mass median aerodynamic diameter that is greater than or equal to 15 microns, in particular greater than 30 microns, more particularly greater than 50 microns, yet more particularly greater than 60 microns, and even more particularly greater than 70 microns.

Advantageously, the second aerosol has a maximum mass median aerodynamic diameter that is less than 300 microns, in particular less than 200 microns, yet more particularly less than 100 microns.

Preferably, the first aerosol comprises a pulmonary deliverable active component.

Conveniently, the first aerosol has a mass median aerodynamic diameter less than or equal to 10 microns, preferably less than 8 microns, more preferably less than 5 microns, yet more preferably less than 1 micron.

Advantageously, the consumable is a cartomiser.

According to a further aspect of the invention, a substitute smoking system is provided, including: an active aerosol generator for generating a first aerosol from a first aerosol precursor, and; a passive aerosol generator for generating a second aerosol from a second aerosol precursor.

According to a further aspect of the invention, a consumable for a substitute smoking device is provided, the consumable including: an airflow passage between an upstream inlet of the consumable and a downstream outlet of the consumable, and; an aerosol generator for generating an aerosol; an external portion of the aerosol generator is located at the outlet of the consumable.

Preferably, the downstream outlet is located at a mouthpiece portion of the consumable.

Conveniently, the aerosol generator is a passive aerosol generator.

Advantageously, the aerosol generation includes a porous member.

Preferably, the external portion is visible to a user of the consumable.

Conveniently, the consumable includes a nozzle surrounding the outlet.

Advantageously, the consumable is a flavour pod.

Preferably, the consumable further including an active aerosol generator for generating a first aerosol.

Conveniently, the first aerosol is sized for pulmonary penetration and the aerosol from the porous member is sized to inhibit pulmonary penetration.

Advantageously, the aerosol from the porous member is transmissible within at least one of: a mammalian oral cavity and a mammalian nasal cavity, and the aerosol from the porous member comprising an active component for activating at least one of: one or more taste receptors in said oral cavity and one or more olfactory receptors in said nasal cavity.

Preferably, the aerosol from the porous member is at least one of: sized to inhibit penetration to the trachea; sized to inhibit penetration to the larynx; sized to inhibit penetration to the laryngopharynx; and sized to inhibit penetration to the oropharynx.

Conveniently, the aerosol from the porous member has a mass median aerodynamic diameter that is greater than or equal to 15 microns, in particular greater than 30 microns, more particularly greater than 50 microns, yet more particularly greater than 60 microns, and even more particularly greater than 70 microns.

Advantageously, the aerosol from the porous member has a maximum mass median aerodynamic diameter that is less than 300 microns, in particular less than 200 microns, yet more particularly less than 100 microns.

Preferably, said first aerosol comprises a pulmonary deliverable active component.

Conveniently, the first aerosol has a mass median aerodynamic diameter less than or equal to 10 microns, preferably less than 8 microns, more preferably less than 5 microns, yet more preferably less than 1 micron.

Advantageously, the consumable is a cartomiser.

According to a further aspect of the invention, a substitute smoking system is provided, including: an airflow passage between an upstream inlet of a component of the system and a downstream outlet of the component, and; an aerosol generator for generating an aerosol; an external portion of the aerosol generator is located at a downstream mouthpiece outlet of the component.

According to a further aspect of the invention, a consumable for a substitute smoking device is provided, the consumable including: an airflow passage between an upstream inlet of the consumable and a downstream outlet of the consumable; an aerosol generator for generating an aerosol at an aerosol generation location, and; wherein the aerosol generation location is substantially at the outlet located at a mouthpiece of the consumable.

Locating the aerosol generation location closer to the outlet of the mouthpiece reduces condensation of the aerosol in the consumable, due to the aerosol travelling a shorter distance within the consumable. This reduces leakage of liquid from the outlet (e.g. into a user's pocket).

Preferably, the aerosol generation location is less than 3 centimetres from the outlet of the consumable.

Conveniently, the aerosol generation location is less than 1.5 centimetres from the outlet of the consumable.

Advantageously, the aerosol generation location is less than 1 centimetre from the outlet of the consumable.

Preferably, the aerosol generation location is less than 0.5 centimetres from the outlet of the consumable.

Conveniently, the aerosol generation location is less than 0.1 centimetres from the outlet of the consumable.

Advantageously, the aerosol generator is a passive aerosol generator.

Preferably, the passive aerosol generator includes a porous member.

Conveniently, the aerosol generator is a passive aerosol generator, and the aerosol generation location is a passive aerosol generation location, and the consumable further including: an active aerosol generator for generating a first aerosol at an active aerosol generation location.

Advantageously, the active aerosol generation location is located upstream from the passive aerosol generation location.

Preferably, the active aerosol generation location is located greater than 2 cm from the outlet of the consumable.

Conveniently, the consumable further including an active aerosol generator for generating a first aerosol.

Advantageously, the first aerosol is sized for pulmonary penetration and the aerosol from the porous member is sized to inhibit pulmonary penetration.

Preferably, the aerosol from the porous member is transmissible within at least one of: a mammalian oral cavity and a mammalian nasal cavity, and the aerosol from the porous member comprising an active component for activating at least one of: one or more taste receptors in said oral cavity and one or more olfactory receptors in said nasal cavity.

Conveniently, the aerosol from the porous member is at least one of: sized to inhibit penetration to the trachea; sized to inhibit penetration to the larynx; sized to inhibit penetration to the laryngopharynx; and sized to inhibit penetration to the oropharynx.

Advantageously, the aerosol from the porous member has a mass median aerodynamic diameter that is greater than or equal to 15 microns, in particular greater than 30 microns, more particularly greater than 50 microns, yet more particularly greater than 60 microns, and even more particularly greater than 70 microns.

Preferably, wherein aerosol from the porous member has a maximum mass median aerodynamic diameter that is less than 300 microns, in particular less than 200 microns, yet more particularly less than 100 microns.

Conveniently, said first aerosol comprises a pulmonary deliverable active component.

Advantageously, the first aerosol has a mass median aerodynamic diameter less than or equal to 10 microns, preferably less than 8 microns, more preferably less than 5 microns, yet more preferably less than 1 micron.

According to a further aspect of the invention, a substitute smoking system is provided, including: an airflow passage between an upstream inlet of a component of the system and a downstream outlet of the component; an aerosol generator for generating an aerosol at an aerosol generation location; wherein the aerosol generation location is substantially at the outlet of the component.

According to a further aspect of the invention, a consumable for a substitute smoking device, the consumable including: an airflow passage between an upstream inlet of the consumable and a downstream outlet of the consumable; an aerosol generator; wherein the outlet is located at a mouthpiece portion of the consumable; the mouthpiece portion including a nozzle for control of an aerosol from the aerosol generator.

Preferably, the nozzle is a divergent nozzle.

Conveniently, a diameter of the nozzle increases in a direction downstream from the outlet.

Advantageously, the outlet is located within the nozzle, the outlet being located adjacent to a position at which the nozzle has the smallest diameter.

Preferably, the nozzle is located downstream of the outlet.

Conveniently, the nozzle has a conical profile.

Advantageously, the nozzle has a trumpet-shaped profile.

Preferably, the nozzle has a bell-shaped profile.

Conveniently, the nozzle is a portion of a housing of the consumable.

Advantageously, the nozzle has an opening angle of between 30 and 60 degrees.

Preferably, the nozzle includes a tapered internal wall and a peripheral rim.

Conveniently, the aerosol generator is a passive aerosol generator.

Advantageously, the passive aerosol generator includes a porous member.

Preferably, the consumable including an active aerosol generator for generating a first aerosol.

Conveniently, the first aerosol is sized for pulmonary penetration and the aerosol from the porous member is sized to inhibit pulmonary penetration.

Advantageously, the aerosol from the porous member is transmissible within at least one of: a mammalian oral cavity and a mammalian nasal cavity, and the aerosol from the porous member comprising an active component for activating at least one of: one or more taste receptors in said oral cavity and one or more olfactory receptors in said nasal cavity.

Preferably, the aerosol from the porous member is at least one of: sized to inhibit penetration to the trachea; sized to inhibit penetration to the larynx; sized to inhibit penetration to the laryngopharynx; and sized to inhibit penetration to the oropharynx.

Conveniently, the aerosol from the porous member has a mass median aerodynamic diameter that is greater than or equal to 15 microns, in particular greater than 30 microns, more particularly greater than 50 microns, yet more particularly greater than 60 microns, and even more particularly greater than 70 microns.

Advantageously, the aerosol from the porous member has a maximum mass median aerodynamic diameter that is less than 300 microns, in particular less than 200 microns, yet more particularly less than 100 microns.

Preferably, said first aerosol comprises a pulmonary deliverable active component.

Conveniently, the first aerosol has a mass median aerodynamic diameter less than or equal to 10 microns, preferably less than 8 microns, more preferably less than 5 microns, yet more preferably less than 1 micron.

Advantageously, the consumable is a cartomiser.

According to a further aspect of the invention, a substitute smoking system is provided, including: an airflow passage between an upstream inlet of a component of the system and a downstream outlet of the component; an aerosol generator; wherein the outlet is located at a mouthpiece portion of the component; the mouthpiece portion including a nozzle for control of an aerosol from the aerosol generator.

According to a further aspect of the invention, there is provided an aerosol delivery device comprising: a first aerosol generator to generate a first aerosol from a first aerosol precursor and to introduce said first aerosol into a first fluid flow pathway, wherein said first aerosol is sized for pulmonary penetration; a second aerosol generator to generate a second aerosol from a second aerosol precursor and to introduce the second aerosol into a second fluid flow pathway, wherein the second aerosol is sized to inhibit pulmonary penetration; wherein the second aerosol is transmissible within at least one of: a mammalian oral cavity and a mammalian nasal cavity, and the second aerosol comprising an active component for activating at least one of: one or more taste receptors in said oral cavity and one or more olfactory receptors in said nasal cavity.

Advantageously, the second aerosol is at least one of: sized to inhibit penetration to the trachea; sized to inhibit penetration to the larynx; sized to inhibit penetration to the laryngopharynx; and sized to inhibit penetration to the oropharynx.

Advantageously, the second aerosol has a mass median aerodynamic diameter that is greater than or equal to 15 microns, in particular greater than 30 microns, more particularly greater than 50 microns, yet more particularly greater than 60 microns, and even more particularly greater than 70 microns.

Advantageously, the second aerosol has a maximum mass median aerodynamic diameter that is less than 300 microns, in particular less than 200 microns, yet more particularly less than 100 microns.

Advantageously, said first aerosol precursor comprises components such that the first aerosol comprises a pulmonary deliverable active component.

Advantageously, the first aerosol has a mass median aerodynamic diameter less than or equal to 10 microns, preferably less than 8 microns, more preferably less than 5 microns, yet more preferably less than 1 micron.

Advantageously, said first aerosol generator is configured to heat said first aerosol precursor.

Advantageously, said first aerosol generator is configured to agitate said first aerosol precursor.

Advantageously, said first fluid flow pathway further receives said first aerosols from a first aerosol inlet of said device.

Advantageously, said first aerosol inlet is configured to inject said first aerosol into said first fluid flow pathway.

Advantageously, said second fluid flow pathway further receives said second aerosol from a second aerosol inlet of said device.

Advantageously, said second aerosol inlet is configured to inject said second aerosols into said second fluid flow pathway.

Advantageously, said first fluid pathway and said second fluid flow pathway merge together.

Advantageously, said first fluid pathway and said second fluid flow pathway are contiguous.

Advantageously, said second fluid flow pathway is disposed along a longitudinal axis of said first fluid flow pathway.

Advantageously, said first fluid flow pathway is disposed proximal to a gas inlet of said device and said second fluid flow pathway is disposed proximal to an aerosol outlet of said device.

Advantageously, said second fluid flow pathway is disposed proximal to a gas inlet of said device and said first fluid flow pathway is disposed proximal to an aerosol outlet of said device.

Advantageously, said second fluid flow pathway is disposed co-axially relative to said first fluid flow pathway.

Advantageously, said second fluid flow pathway is disposed adjacent said first fluid flow pathway in a side by side relationship therewith.

Advantageously, said first fluid flow pathway is separated from said second fluid flow pathway by a wall member.

Advantageously, said first fluid flow pathway comprising a first housing to constrain said fluid flow and said second fluid flow pathway comprising a second housing to constrain said second fluid flow, said first housing to receive said first aerosol; and said second housing to receive said second aerosol.

Advantageously, said first housing comprising said first aerosol generator and/or said second housing comprising said second aerosol generator.

Advantageously, said first housing comprises a removable module of said delivery device.

Advantageously, said first housing comprises a replaceable module of said delivery device.

Advantageously, said first housing comprises a refillable module of said delivery device.

Advantageously, said second housing comprises a removable module of said delivery device.

Advantageously, said second housing comprises a replaceable module of said delivery device.

Advantageously, said second housing comprises a refillable module of said delivery device.

Advantageously, said first aerosol precursor comprises nicotine, or a nicotine derivative, or a nicotine analogue.

Advantageously, said first aerosol precursor comprises a pulmonary deliverable active component that is a free nicotine salt comprising at least one of: nicotine hydrochloride; nicotine dihydrochloride; nicotine monotartrate; nicotine bitartrate; nicotine bitartrate dihydrate; nicotine sulphate; nicotine zinc chloride monohydrate; and nicotine salicylate.

Advantageously, said second aerosol being transmissible to activate at least one of: one or more taste receptors in said oral cavity; and one or more olfactory receptors in said nasal cavity.

Advantageously, said first aerosol generator is configured to generate the first aerosol from a first aerosol precursor comprising at least one of: glycol; polyglycol; and water.

Advantageously, said second aerosol generator is configured to introduce said second aerosol into said fluid flow pathway at a pre-set period of time following an actuation of said first aerosol generator.

Advantageously, said second fluid flow pathway comprises at least one baffle configured such that a portion of said second aerosol impinges on said baffle.

Advantageously, said aerosol inlet port is configured to introduce the second aerosol of a mass median aerodynamic diameter to inhibit pulmonary penetration.

Advantageously, said second aerosol generator comprises a Venturi aperture to dispense and aerosolise the second aerosol precursor in the second aerosol generator, wherein the second aerosol precursor is a liquid.

Advantageously, said second aerosol generator comprises a piezoelectric element to dispense and aerosolise the second aerosol precursor in the second aerosol generator, wherein the second aerosol precursor is a liquid.

Advantageously, said second aerosol generator comprises a precursor substrate for the second aerosol precursor, wherein the precursor substrate comprises a hydrophobic surface.

Advantageously, said second aerosol generator comprises a plurality of capillary tubes configured to draw the second aerosol precursor from a reservoir of second aerosol precursor to a free end of the plurality of capillary tubes.

Advantageously, the free end of the plurality of capillary tubes is hydrophobic.

Advantageously, said first aerosol is of a size suitable for deep lung penetration.

Advantageously, said first aerosol has a mass median aerodynamic diameter less than 2 µm.

Advantageously, said second fluid flow pathway terminates in a second fluid flow pathway mouthpiece.

Advantageously, said first fluid flow pathway terminates in a first fluid flow pathway mouthpiece.

Advantageously, said first and second fluid flow pathways terminate in a combination mouthpiece.

Advantageously, said combination mouthpiece comprises separate pathways corresponding to said first and second fluid flow pathways respectively.

Advantageously, said merged first and second fluid flow pathways terminate in a mouthpiece.

Advantageously, said active component comprises a physiologically active component.

According to a further aspect of the invention, a first fluid pathway housing is provided, the first fluid pathway housing being for an aerosol delivery device according to the first aspect.

Advantageously, the first fluid pathway housing comprises said first aerosol precursor.

Advantageously, the first fluid pathway housing comprises said first aerosol generator.

According to a further aspect of the invention, a second fluid pathway housing is provided, the second fluid pathway housing being for an aerosol delivery device according to the first aspect.

Advantageously, the second fluid pathway housing comprises said second aerosol precursor.

Advantageously, the second fluid pathway housing comprises said second aerosol generator.

According to a further aspect of the invention, a kit of parts is provided, the kits of parts being for an aerosol delivery device according to an aspect of the invention, the kit of parts including a first fluid pathway housing according to another aspect and a second fluid flow pathway housing according to the another aspect.

The invention includes the combination of the aspects and preferred features described except where such a combination is clearly impermissible or expressly avoided.

BRIEF DESCRIPTION OF THE DRAWINGS

One or more specific embodiments in accordance with aspects of the present invention will be described, by way of example only, and with reference to the following drawings in which:

Figures 21, 22:
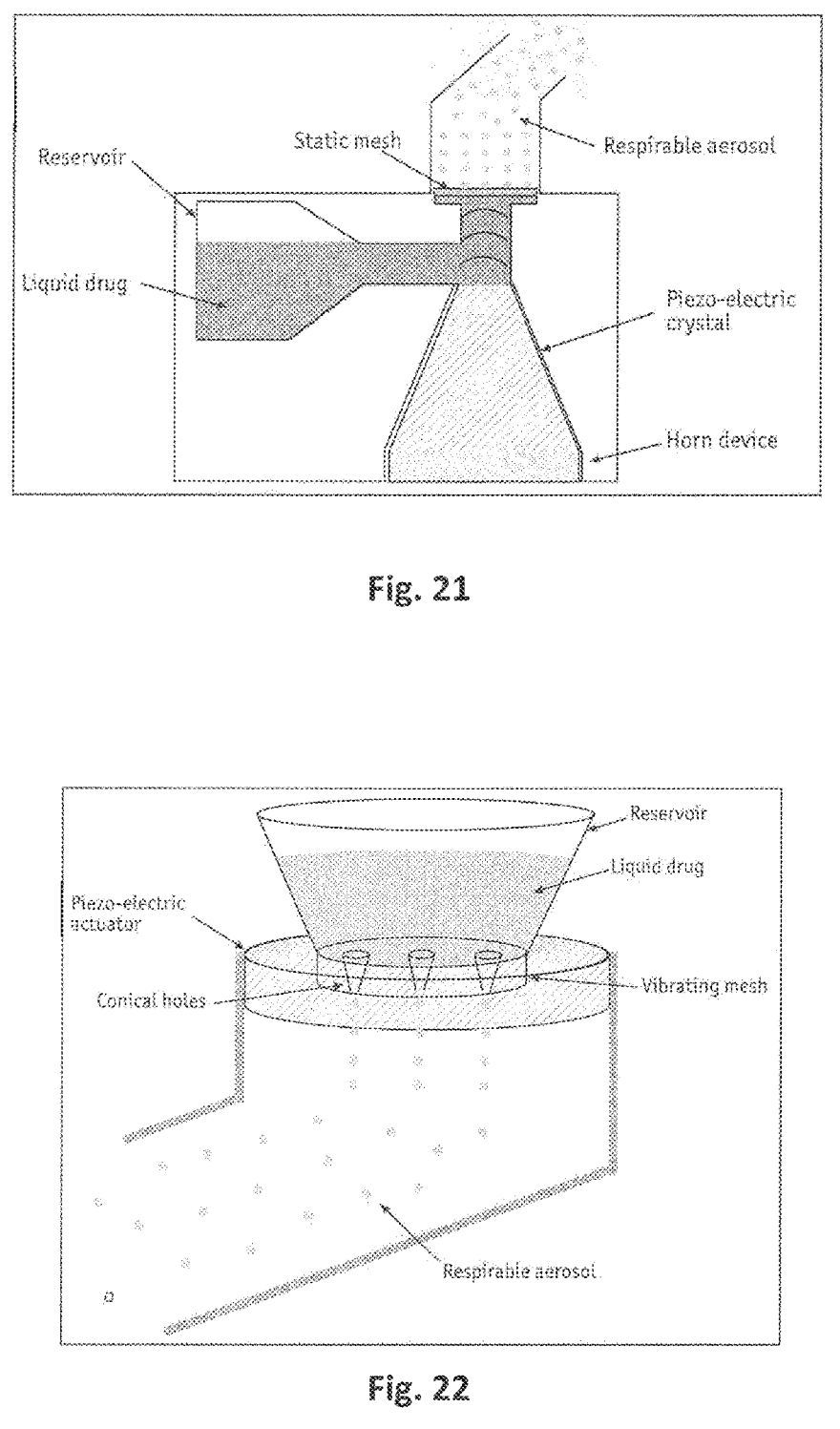

FIG. 21 is a schematic illustration of a static mesh atomiser;

FIG. 22 is a schematic illustration of a vibrating mesh atomiser;

DETAILED DESCRIPTION

Figure 1:
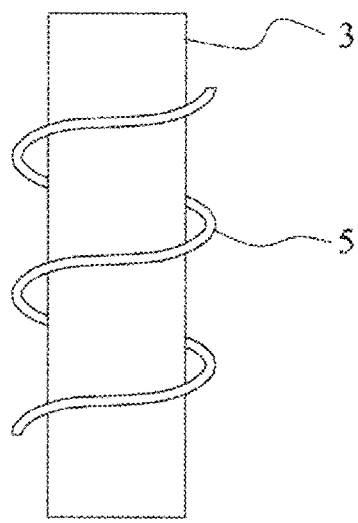
FIG. 1 is a schematic illustration of a heating element for vaping apparatus.

By way of general overview, FIG. 1 shows a schematic illustration of a vapourisation component 1 for a conventional e-cigarette. The vapourisation component comprises a wick 3, which may be solid or flexible, saturated in e-liquid with a heating coil 5 wrapped around it. Hence, the component is generally termed a wick-and-coil heater. In use, an electric current is passed through the coil 5 thereby heating the coil. This heat is transferred to the e-liquid in the wick 3 causing it to evapourate.

Figure 2:
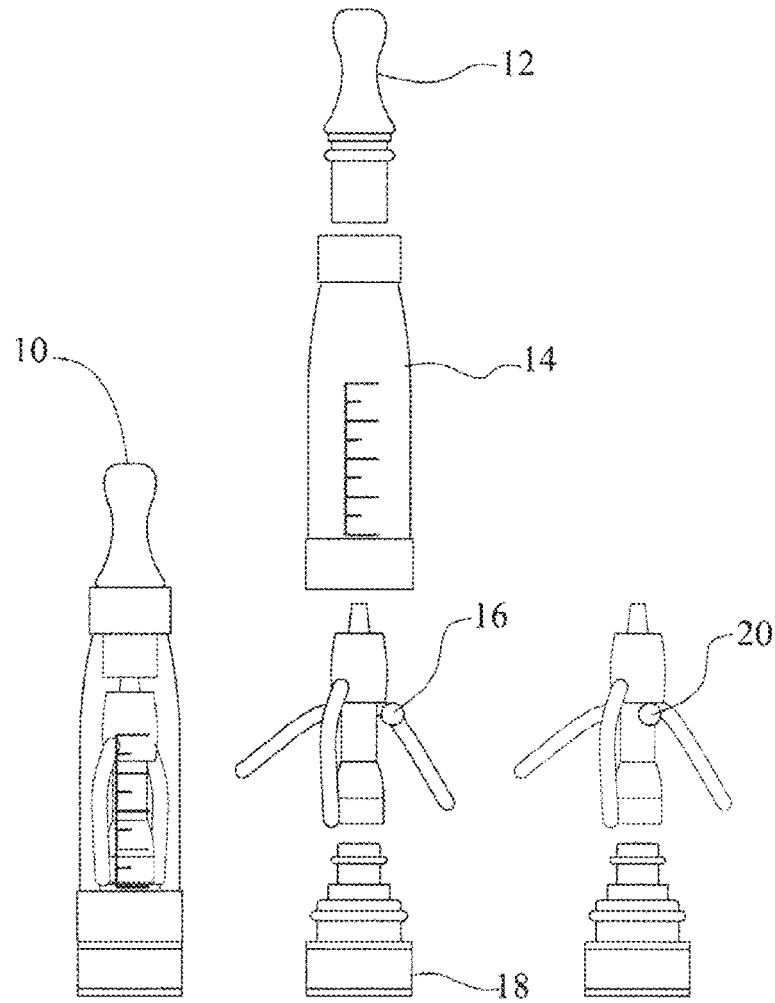
FIG. 2 is an illustration of a clearomiser vaping apparatus.

Smoking substitute devices, such as an e-cigarette, may be refillable to replace consumed e-liquid. An example of the heating, e-liquid reservoir and mouthpiece regions of an e-cigarette 10, known as a clearomiser, is illustrated in FIG. 2. The mouthpiece 12 may be coupled to the clear tank 14 which acts as a reservoir for the e-liquid. The heating arrangement includes a wick 16 which draws e-liquid to a heating element 20. The heating element 20 is powered by a battery coupled through electrical connection 18. E-liquid drawn to heating element 20 is vapourised and forms an aerosol mist which may be drawn into a user's mouth by the user drawing air through mouthpiece 12. The airflow is typically introduced through small inlets in or near the electrical connection 18 and through a central fluid pathway for the airflow which passes over or intimately adjacent the heating element such that vapourised e-liquid may be entrained in the air flow and drawn along the fluid pathway into the mouthpiece 12. Generally, the vapour condenses on the cooler air flow to form an aerosol mist of e-liquid condensate particles. The e-liquid may be flavoured. If a user wishes to change the flavour they have to change the e-liquid in their device which requires the tank for containing the e-liquid to be emptied and replaced with an e-liquid of the desired flavour. Optionally, the user may use a different device, or interchangeable tank, with the desired flavour e-liquid loaded into it.

Flavour is experienced by a user through taste and/or olfactory receptors located in their oral and nasal cavities. The inventors have recognised that flavour aerosols may penetrate into the oral and nasal cavities to deliver the flavour component to the user without penetrating any further. However, physiologically active substances such as pharmaceutical compounds and nicotine may be more effectively delivered through the pulmonary system, in particular through deep lung penetration.

Figure 3A:
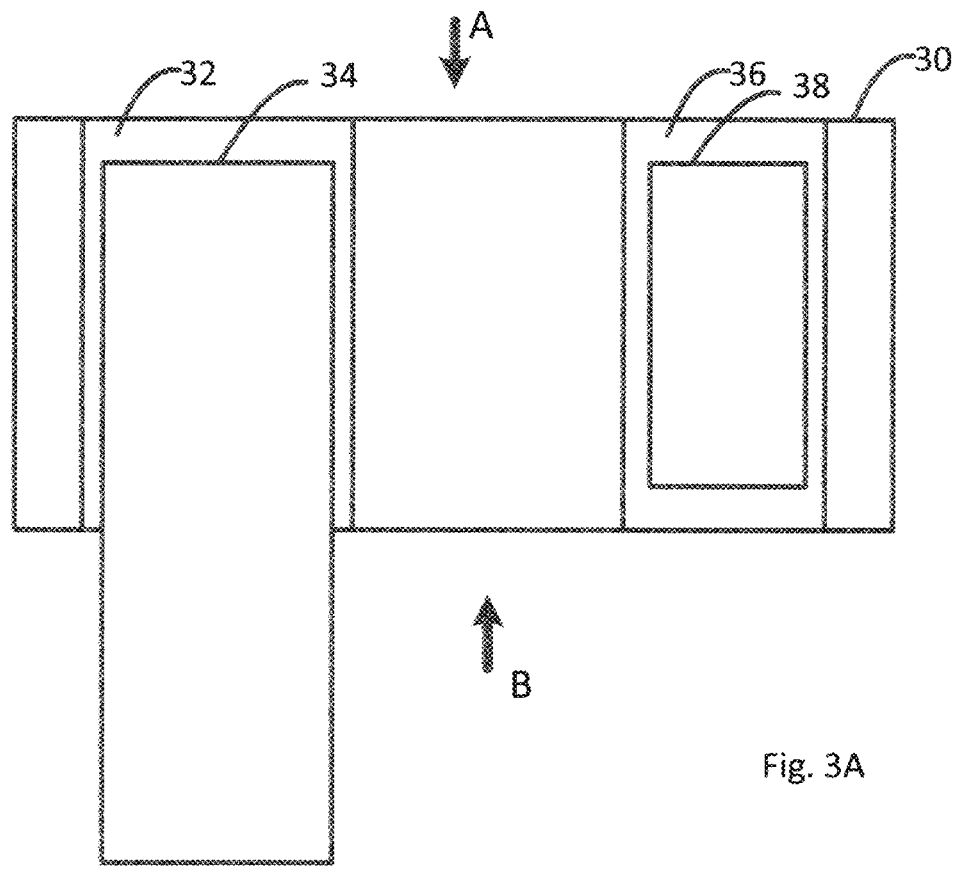
FIG. 3A is a schematic illustration of a cross-section of a mouthpiece in accordance with an embodiment of the present invention.

Turning now to FIG. 3A, there is shown a schematic illustration of a mouthpiece unit 30 which may be utilised to deliver flavour separately from an active component such as nicotine utilising a vaping apparatus. The mouthpiece 30 comprises an open-ended hollow cylindrical section 32 which is configured to receive a mouthpiece or "drip tip" 12 of a vaping unit 34 such as a clearomiser as illustrated in FIG. 2 and to provide a fluid pathway. A second open-ended hollow cylindrical section 36 is configured to receive a "flavour" element 38 and to provide a fluid pathway. The flavour element 38 is a substrate which supports a flavour component aerosol precursor typically in a liquid form such as a "Blueberry" flavour trade name FQ C036 E-FLAVOUR BLUEBERRY supplied by Hertz Flavors GmbH & CO. KG of Reinbek, Germany. The flavour element 38 comprises a matrix to support the flavour component and through which air can be drawn from side "B" to side "A". The airflow through flavour element 38 causes aerosols of the flavour component to be formed and entrained in the airflow to be carried to side A.

A user is to place the mouthpiece 30 into their mouth with side B protruding from their mouth and to draw air to side A from side B to cause an airflow from side B through the flavour element 38 and consequently to draw flavour aerosols into the user's mouth. The user may activate the vaping apparatus 34 to generate an aerosol mist from the e-liquid precursor in the vaping apparatus by drawing air on the A side of mouthpiece 30. By activating the vaping apparatus 34 while drawing air through mouthpiece 30 a user will take both aerosols from the vaping apparatus containing an active component and flavour aerosols from flavour element 38.

Figure 3B:
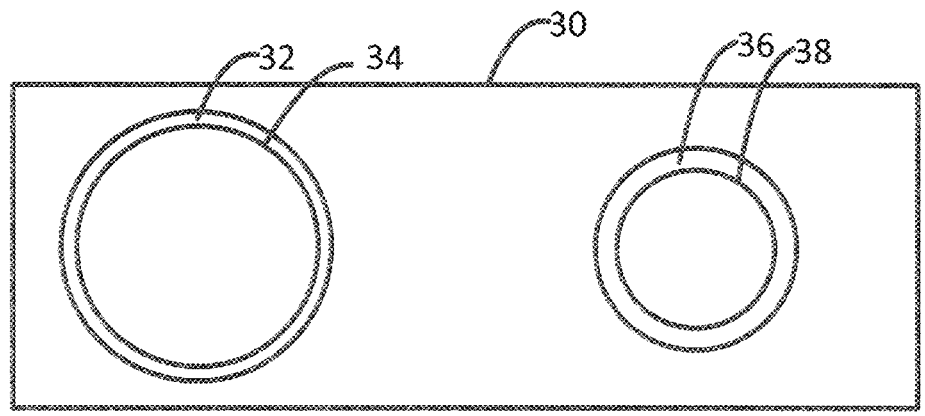
FIG. 3B is a schematic illustration of a cross-section of the mouthpiece illustrated in FIG. 3A a plane perpendicular to the plane of the cross-section illustrated in FIG. 3A.

FIG. 3B schematically illustrates mouthpiece 30 viewed from side A. Although the vaping apparatus 34 is shown to be spaced apart from the inner wall of hollow cylinder 32, that is to improve the clarity of disclosure and to clearly illustrate the respective components. In practice vaping apparatus will engage with mouthpiece 30 typically by way of a sliding friction fit. Likewise for flavour element 38 and hollow cylinder 36.

The aerosols generated in vaping apparatus 34 are formed by the heating of a vapour pre-cursor liquid such that they are typically of a size with a mass median aerodynamic diameter less than or equal to 10 microns, preferably less than 8 microns, more preferably less than 5 microns, yet more preferably less than 1 microns. Such sized aerosols tend to penetrate into a human user's pulmonary system. The smaller the aerosol the more likely it is to penetrate deeper into the pulmonary system and the more effective the transmission of the active component into the user's blood stream. Such deep lung penetration is something that is desirable for the active component but unnecessary for the flavour component. The flavour component may enter a user's oral and or nasal cavities in order to activate taste and or olfactory receptors and not penetrate the pulmonary system.

The flavour component is configured such that it is typically forms an aerosol with a mass median aerodynamic diameter that is greater than or equal to 15 microns, in particular, greater than 30 microns, more particularly greater than 50 microns, yet more particularly greater than 60 microns, and even more particularly greater than 70 microns. Without being bound by any theory, such a size of aerosol may be formed by drawing liquid droplets from a substrate at the ambient temperature of a user's environment, e.g. room temperature, by an airflow over the substrate. The size of aerosol formed without heating is typically smaller than that formed by condensation of a vapour. The size of the aerosols formed without heating such as drawing air over a substrate supporting the liquid may be influenced by the ambient temperature, the viscosity and or density of the liquid. However, it is generally, and most likely to be the case, that aerosols formed without heating are of a considerably larger size than those formed through heating. The flavour aerosols may be formed with a maximum mass median aerodynamic diameter that is less than 300 microns, in particular less than 200 microns, yet more particularly less than 100 microns. Such a range of mass median aerodynamic diameter will produce aerosols which are sufficiently small to be entrained in an airflow caused by a user drawing air through the flavour element 38 and to enter and extend through the oral and or nasal cavity to activate the taste and/or olfactory receptors.

As a brief aside, it will be appreciated that the mass median aerodynamic diameter is statistical measurement of the size of the particles/droplets in an aerosol. That is, the mass median aerodynamic diameter quantifies the size of the droplets that together form the aerosol. The mass median aerodynamic diameter may be defined as the diameter at which 50% of the particles/droplets by mass in the aerosol are larger than the mass median aerodynamic diameter and 50% of the particles/droplets by mass in the aerosol are smaller than the mass median aerodynamic diameter. The "size of the aerosol", as may be used herein, refers to the size of the particles/droplets that are comprised in the particular aerosol. The size of the particles/droplets in the aerosol may be quantified by the mass median aerodynamic diameter, for example.

The size of the aerosol generated by an aerosol generator may depend on, for example, the temperature of the liquid precursor, the density of the liquid precursor, the viscosity of the liquid precursor, or a combination. The size of the aerosol generated by an aerosol generator may also depends on the particular parameters and configuration of the aerosol generating apparatus, which are described in more detail below.

Flavour element 38 may be formed of any suitable porous material for providing the substrate. For example, it may be formed of a material typically used as a filter for a cigarette or the substrate material for a Nicorette Inhalator™, i.e. a porous polypropylene or polyethylene terephthalate. A liquid flavour component may then be dripped on to the flavour element 38. Flavour element 38 substrate may comprise a porous material where pores of the porous material hold, contain, carry, or bear a flavour compound. Optionally or additionally, the porous material may comprise a sintered material such as, for example, BioVyon™ (by Porvair Filtration Group Ltd).

Figure 4:
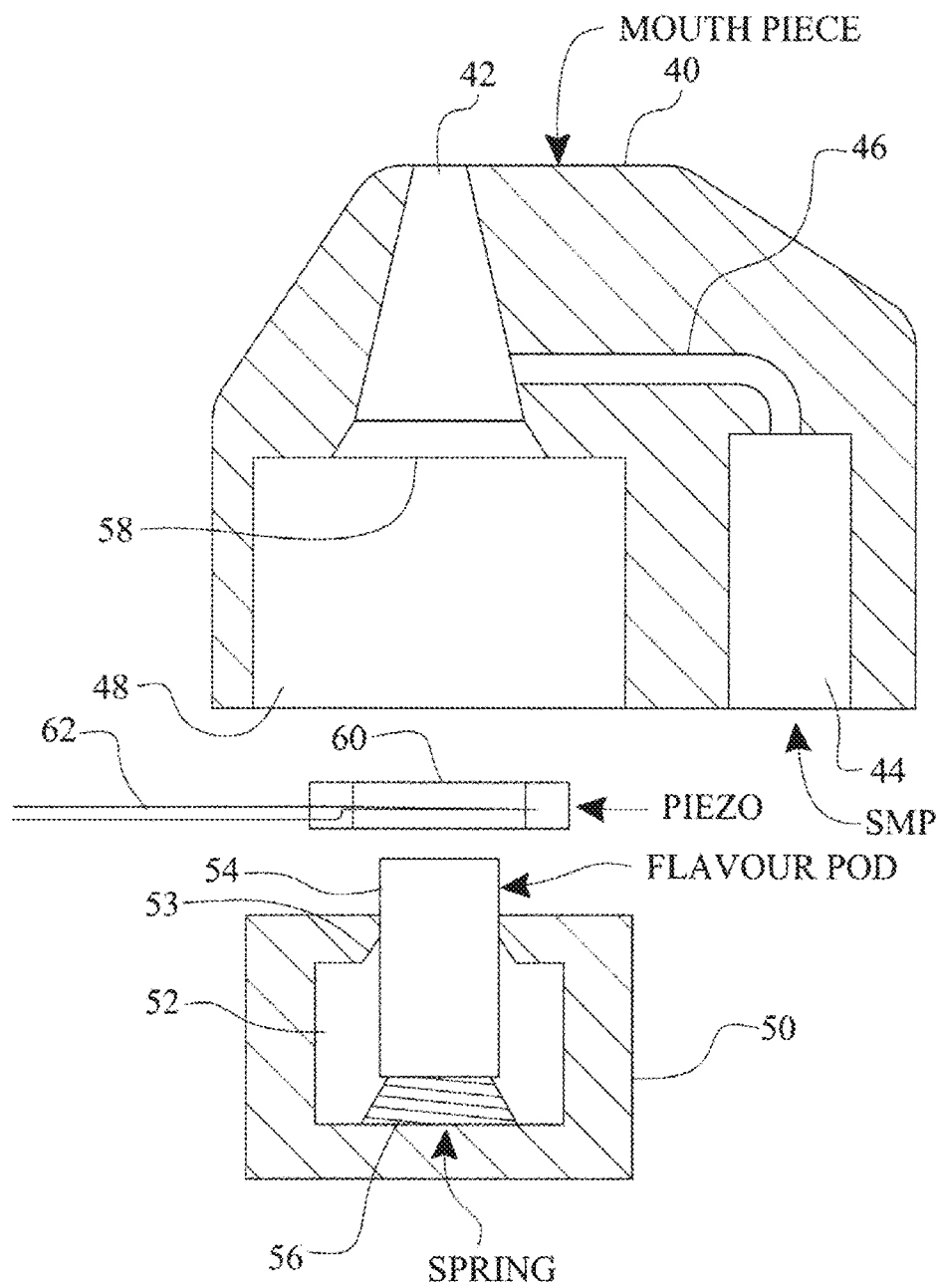
FIG. 4 is a schematic illustration of a mouthpiece in accordance with an embodiment of the present invention illustrating a piezoelectric aerosol generator.

In the embodiment illustrated in FIG. 4 the mouthpiece 40 is shaped to fit to a user's mouth in a conventional configuration for a mouthpiece. A tapered fluid flow pathway 42 terminates at the mouth end of piece 40 and is coupled to a cavity 44 for receiving a vaping apparatus by a fluid flow pathway 46. A cavity 58 is configured to receive a flavour pod 50 which holds a flavour element 54. The flavour pod 50 has a cavity 52 with an opening 53 sized to permit insertion of flavour element 54 into cavity 52. Cavity 52 also houses a helical spring 56. Helical spring 56 is disposed at one end of cavity 52 opposite opening 53.

Flavour element 54 is disposed in flavour pod 50 so as to rest on helical spring 56. A piezo-electric vibration unit 60 is disposed in contact with an end of flavour element 54 and is powered through electrical connection 62. Piezo-electric element 60 comprises a piezo-electric crystal electrically couplable to a power supply, such as an electrical battery, through connection 62. The piezo-electric element 60 includes a perforated membrane vibrated by a piezo-electric crystal or formed of the piezo-electric crystal itself. The perforations in the vibratable membrane form small droplets of liquid flavour component adsorbed in flavour element 54 when the membrane is vibrated. The vibration is typically in the range 100 kHz to 2.0 MHz, in particular between 108 kHz and 160 kHz, and more particularly at substantially 108 kHz, for example. Such vibration frequencies may be used to form aerosols of the liquid flavour component which may be drawn by airflow from the flavour element 54 to the terminal end of mouthpiece 50 and are of a size as set out in the ranges above.

Electrical connection 62 may be coupled to a power supply through a switch operative by a user or responsive to a pressure drop in the fluid pathway 42/cavity 58 as a user draws air from the mouthpiece 40. Optionally, electrical connection 62 may be coupled through a switch on the vape apparatus (SMP) so that the piezo-electric element 60 is actuated when a user actuates the vape apparatus.

Figure 11:
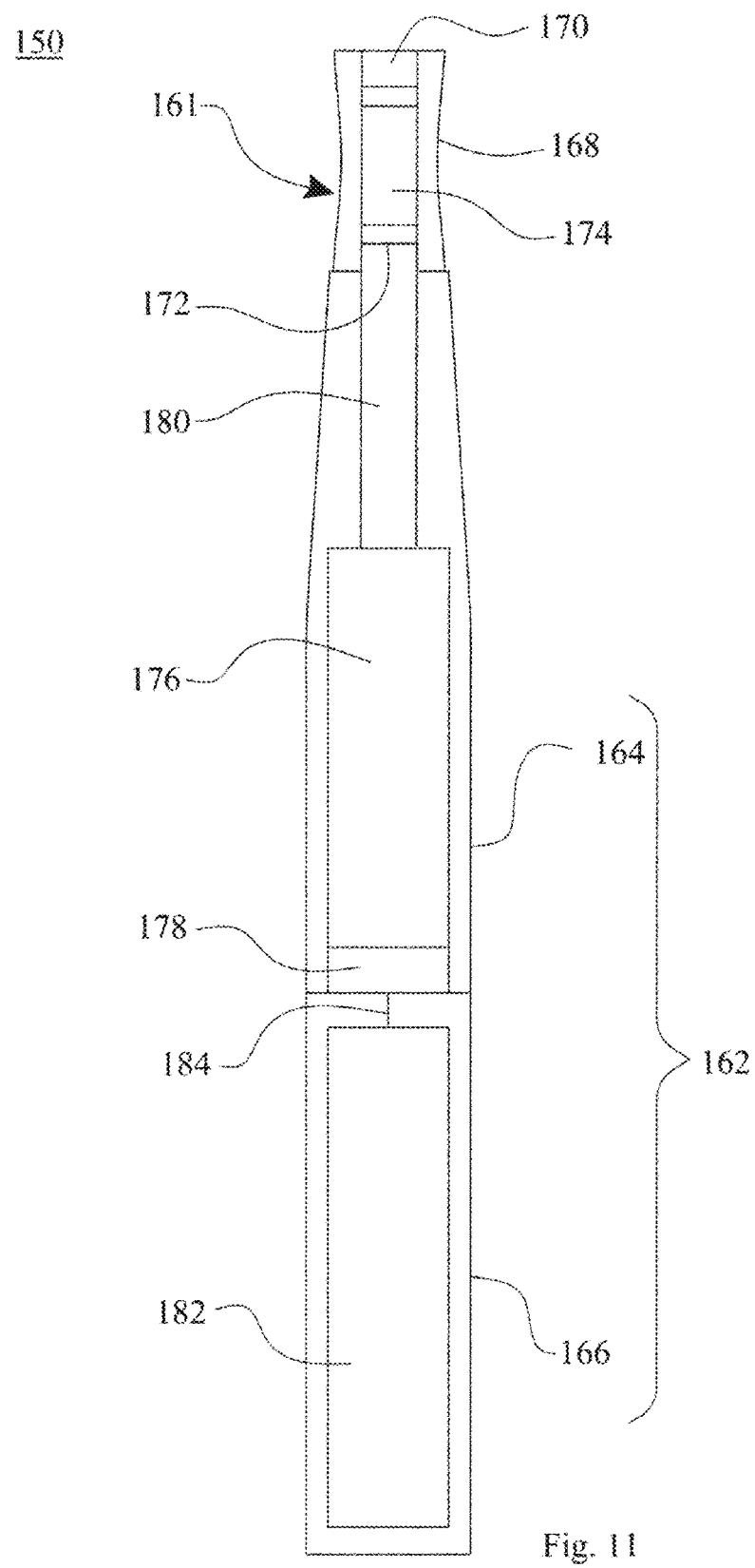
FIG. 11 is a cross-sectional side view illustration of a device in accordance with an embodiment of the present invention.
Figure 12:
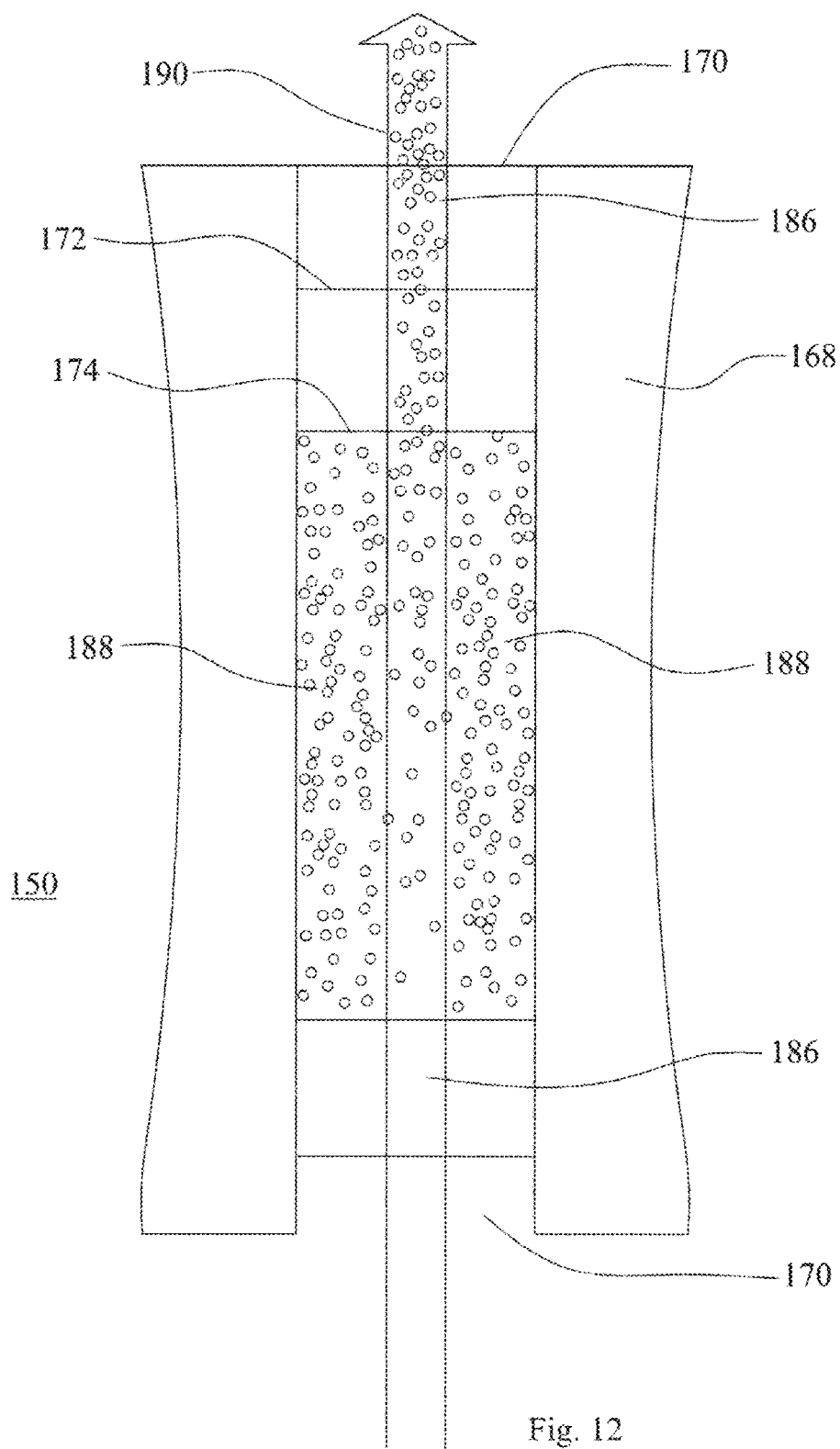
FIG. 12 is a cross-sectional side view illustration of a vapour outlet conduit of the system and device for nicotine delivery of FIGS. 1 and 2 according to one or more embodiments of the present invention.

Another configuration for apparatus which comprises separate flavour and nicotine aerosol delivery is illustrated in FIG. 11 and FIG. 12.

For the avoidance of doubt, in the following description of FIG. 11 and FIG. 12 the term "upstream" defines a position towards the point at which a fluid will be drawn into the aerosol outlet conduit 168 when the apparatus is in use, i.e. a point from which air containing aerosols is drawn into an aerosol outlet conduit 168 from atmosphere and/or from the aerosol generation unit 162. The term "downstream" defines a position from the point at which fluid containing flavour exits the flavour element 172. Based on these definitions, any fluid in the fluid passage 170 that is "upstream" of the flavour element 172 does not contain any flavour component and any fluid in the fluid passage that is "downstream" of the carrier unit 172 may contain flavour (dependent upon whether or not the flavour element 172 contains a liquid flavour component and/or a flavour compound and the extent to which the flavour component is drawn into the fluid as it traverses the carrier unit 172).

A cross-sectional side view of the apparatus 150 is schematically illustrated in FIG. 11. As can be seen in FIG. 11, the flavour element 172 contains a substrate 174, which, in one or more embodiments, is impregnated with a liquid flavour component and/or a flavour compound. Optionally, the substrate 174 may comprise a porous material where pores of the porous material hold the liquid flavour component and/or the flavour compound. Further optionally, the porous material may comprise a sintered polymer such as, for example, BioVyon™ (by Porvair Filtration Group Ltd). The porous material of substrate 174 is configured for "wicking" or "drawing" nicotine precursor material away from end regions of the substrate 14 (i.e. toward a centre region of the substrate 174). This may prevent leakage of the liquid flavour component from the substrate (and thus from the carrier unit 172 when penetrable films (not shown in FIG. 11-FIG. 12) sealing the flavour element are broken). Thus, liquid flavour component may be held within the substrate 174 until airflow therethrough (i.e. during use) causes aerosolisation and creates aerosols of flavour from the liquid flavour component.

Vapouriser portion 164 of aerosol generation unit 162 comprises a reservoir 176 configured to contain a vapour precursor material, a vapourising arrangement 178 configured to vapourise the vapour precursor material and a fluid flow pathway passage 180 for delivery of aerosols formed from the vapour precursor material to the fluid flow pathway passage 170 of the aerosol outlet conduit 168.

The vapour precursor material may be in liquid form and may comprise one or more of glycol, polyglycol, propylene glycol and water.

The vapourising arrangement 178 comprises a chamber (not shown) for holding vapour precursor material received from the reservoir 176 and a heating element (not shown) for heating vapour precursor material in the chamber.

The vapourising arrangement 178 further comprises a conduit (not shown) in fluid communication with the chamber and configured to deliver aerosols formed from heated vapour precursor material in the chamber to the vapour passage 180.

The vapourising arrangement 178 further comprises control circuitry (not shown) operative by a user, or upon detection of air and/or aerosols being drawn though the aerosol outlet conduit 168, i.e. when the user sucks or inhales.

Battery portion 166 of the aerosol creation system 162 comprises a battery 182 and a coupling 184 for mechanically and electrically coupling the battery portion 166 to the vapouriser portion 164. When the battery portion 166 and vapouriser portion 164 are coupled as shown in FIG. 11, battery 182 is electrically coupled to the vapourising arrangement 178 to supply power thereto.

Responsive to activation of the control circuitry of vapourising arrangement 178, the heating element heats vapour precursor material in the chamber of the vapourising arrangement 178. Vapour formed as a result of the heating process forms an aerosol of liquid condensate which passes through the conduit into the fluid pathway passage 180 of the vapouriser portion 164. This aerosol comprising fluid then passes into an upstream region of aerosol fluid pathway 170 of the aerosol outlet conduit 168, through the flavour element 172, where flavour from the substrate 174 becomes entrained in the aerosol stream, and then onwards through the downstream region of aerosol fluid pathway 170 for delivery to the user.

This process is illustrated in FIG. 12, where arrow 186 schematically denotes the flow of the aerosol fluid stream from the aerosol passage of the vapouriser portion to the upstream region of aerosol fluid pathway 170 of the vapour outlet conduit 168, through the flavour element 172, and then through the downstream region of aerosol fluid pathway 170 for delivery to the user.

FIG. 12 also schematically illustrates flavour and/or flavour compounds 188 contained in the substrate 174 and the flavour and/or flavour compounds passing from the substrate 174 into the aerosol fluid stream 186, i.e. becoming entrained in the aerosol stream 186. Flavour and/or flavour compounds within the aerosol stream 186 are denoted by reference numeral 190.

Figure 5:
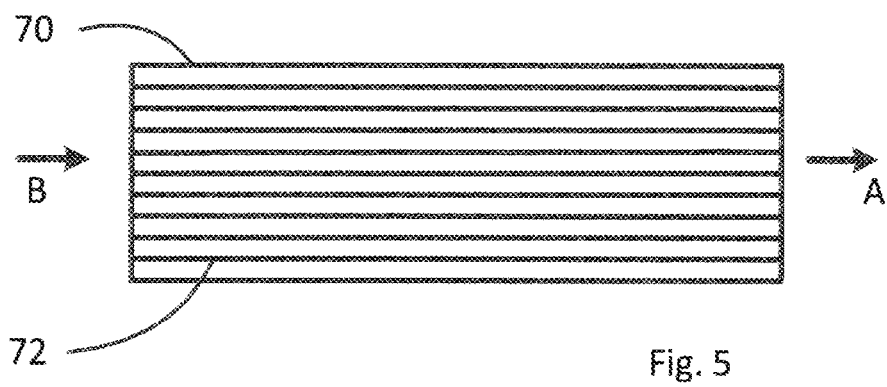
FIG. 5 is a schematic illustration of a flavour element for generating flavour aerosols in accordance with an embodiment of the present invention.

FIG. 5 is a schematic illustration of another embodiment in which a flavour element 70 provides a substrate for a liquid flavour component in which the substrate is laminar in structure having a series of laminates 72. An airflow drawn from side B traverses the laminar structures and generates an aerosol of the liquid flavour component which becomes entrained in the airflow and carried to side A to a user's mouth. A flavour element 70 may be disposed in a mouthpiece 30 such as illustrated in and described with reference to FIG. 3A and FIG. 3B or mouthpiece 40 as illustrated in and described with reference to FIG. 4.

Flavour element 70 may also be disposed in apparatus 150 in place of the flavour element 172 illustrated in FIG. 11 and FIG. 12.

Figure 6:
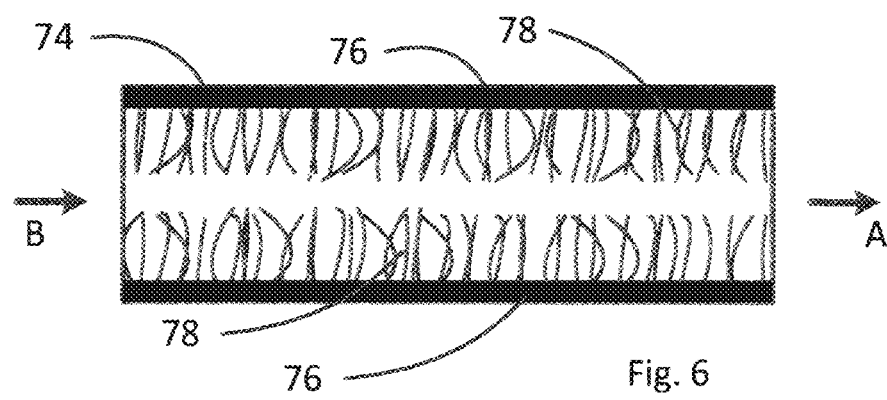
FIG. 6 is a schematic illustration of a flavour element for generating flavour aerosols in accordance with an embodiment of the present invention.

FIG. 6 is a schematic illustration of a further embodiment in which a flavour element 74 is formed of a hollow tubular section having open-ended capillary filaments 76 extending from an interior wall 78 of the tube. The capillary elements may be filled with a liquid flavour component. Air flow through the tube, illustrated by non-limiting example as from end B to end A, creates a pressure drop over a free open end of one or more of the capillary elements 76 causing droplets of the liquid flavour component to be drawn from the open end of the capillary elements and entrained in the airflow from B to A. Optionally, wall 78 may include a reservoir of liquid flavour component into which capillary filaments 76 are inserted into and or extend from to draw liquid flavour component from such a reservoir to the free open end of the capillary filaments 76. The reservoir may be a suitable matrix formed of a porous material and integrated with the wall or formed separately therefrom and inserted into the tube during assembly of the flavour element 74.

The capillary filaments are of a diameter to form aerosol-sized droplets within the ranges set out above. Generally, an open-end aperture of a diameter around the desired median diameter of the aerosol to be generated produces an aerosol of such median diameter. The exact size of the particles/droplets comprised in the aerosol will depend on the surface tension and temperature of the liquid flavour component as well as the pressure exerted on it, amongst other things. In the described embodiment the capillary filaments, or at least there open-end, are of a hydrophobic material in order to generate release of droplets of liquid.

Figure 7:
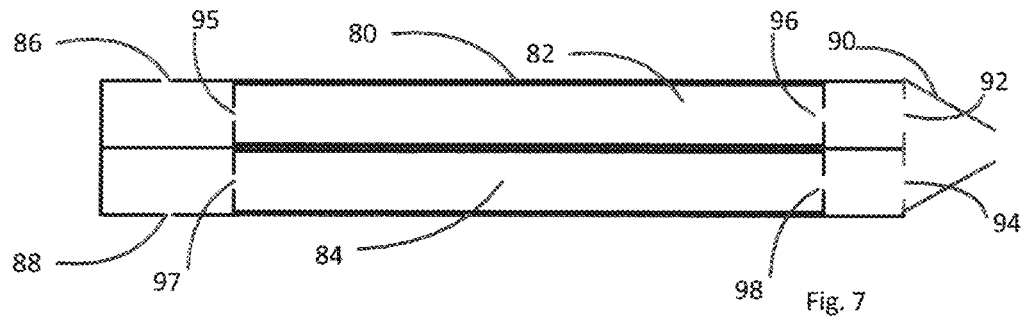
FIG. 7 is a schematic illustration of a device in accordance with an embodiment of the present invention.

In the embodiment schematically illustrated in FIG. 7 respective aerosol generators are disposed in side-by-side relationship in the apparatus 80. A flavour aerosol generator 82 and an active component aerosol generator 84 are illustrated in side-by-side relationship. Air may be drawn into flavour aerosol generator 82 from external air hole 86 and into flavour aerosol generator 82 through air hole 95. In a similar fashion air is drawn into active component generator 84 through external air hole 88 and into active component aerosol generator through air hole 97. Aerosol laden fluid exits the flavour aerosol generator 82 and active component aerosol generator 84 through outlet apertures 96 and 98 respectively. Outlet apertures 96 and 98 provide fluid communication to mouthpiece 90 through apertures 92 and 94. Mouthpiece 90 creates a plenum chamber in which the aerosols may be mixed prior to being inhaled by a user. The active component aerosol generator 84 comprises a vapour generator arrangement such as utilised in conventional vaping devices with an electrically powered heater and battery to supply electrical power. Neither details of the heater and battery pack are illustrated in the Figure for convenience and clarity of disclosure.

Figure 8:
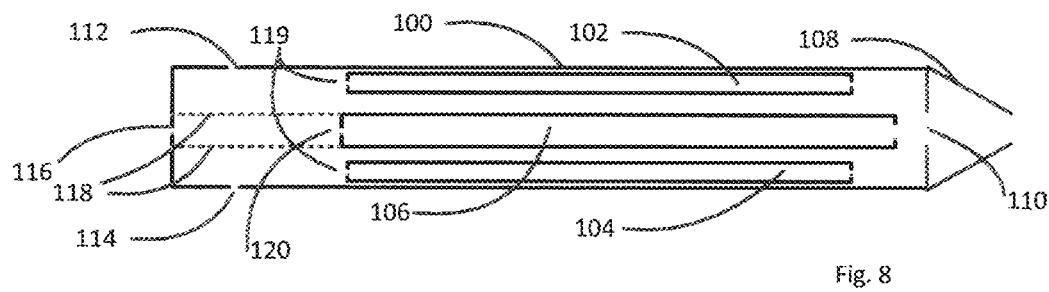
FIG. 8 is a schematic illustration of a device in accordance with an embodiment of the present invention.

A further embodiment in accordance with the present invention is schematically illustrated in FIG. 8 which shows apparatus 100 in which respective aerosol generators 102/104 and 106 are disposed in a concentric configuration. In the described embodiment flavour aerosol generator 102/104 is disposed in a concentric arrangement around the active component aerosol generator 106. Respective reference numerals 102 and 104 serve to illustrate respective parts of the flavour aerosol generator on either side of the active component aerosol generator 106 when the apparatus 100 is shown in cross-section. The apparatus has a mouthpiece 108 disposed at one end. An aperture 110 provides fluid communication from the outputs of the flavour and aerosol generators 102/104 and 106 respectively to mouthpiece 108. Air may be drawn into the aerosol generators through external air inlets 112, 114 and 116. As illustrated, a perforated conduit 118 allows air drawn in through external air inlets 112, 114 and 116 to be drawn into any one of the aerosol generators to aerosol generator airing at 119 and 120. In an optional embodiment, conduit 118 is not perforated and the respective airflow is kept apart. Likewise as for the embodiment illustrated in FIG. 7, the active component aerosol generator 106 comprises a generator as typically found in conventional vaping apparatus.

In an optional embodiment, active component aerosol generator 106 may be disposed in a circumferential arrangement about the flavour aerosol generator 102/104.

Figure 9:
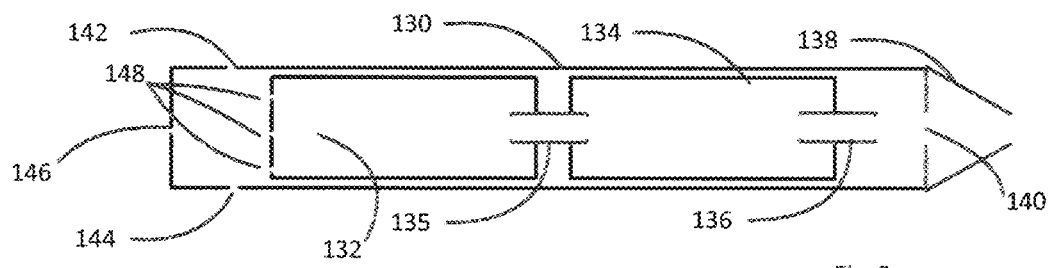
FIG. 9 is a schematic illustration of a device in accordance with an embodiment of the present invention.

FIG. 9 illustrates a yet further embodiment in accordance with the present invention in which the apparatus 130 comprises an in-line arrangement of respective active component aerosol generator 132 and flavour aerosol generator 134. The active component aerosol generator 132 is in fluid communication with the flavour aerosol generator 134 through fluid conduit 135. The fluid pathway through active component aerosol generator 132 and flavour aerosol generator 134 is coupled through fluid conduit 136 to aperture 114 and into mouthpiece 138. Air is drawn into active component aerosol generator 132 from external air inlets 142, 144 and 146 via perforations 148. Likewise as for the embodiment illustrated in FIG. 7, the active component aerosol generator 132 comprises a generator as typically found in conventional vaping apparatus.

Figure 10:
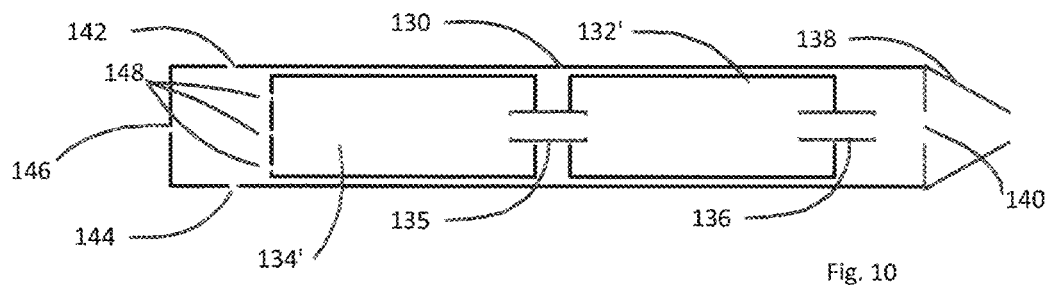
FIG. 10 is a schematic illustration of a device in accordance with an embodiment of the present invention.

In the embodiment schematically illustrated in FIG. 10, a similar arrangement is illustrated in FIG. 9 is disclosed, would like parts referred to with like numerals, but with the active component aerosol generator and flavour aerosol generator reversed. Thus, it is the flavour aerosol generator 134' that is upstream of the active component aerosol generator 132'.

The flavour aerosol generators of any of the embodiments disclosed in FIGS. 7 through to 10 may employ the flavour element configurations as disclosed in FIGS. 3 through to 6 in FIGS. 11 and 12, for example. However, any suitable aerosol generation mechanism may be employed to generate aerosols of the range defined above for the flavour aerosols.

For clarification, the active component aerosol generators in the foregoing and subsequent described embodiments are configured to generate aerosols sized for pulmonary penetration, in particular deep lung penetration, and generally to generate active component aerosols sized to have a mass median aerodynamic diameter less than or equal to 10 microns, preferably less than 8 microns, more preferably less than 5 microns, yet more preferably less than 1 microns. It is the case that aerosols formed from a vapour condensate, i.e. an aerosol mist, such as occurs in a typical E-cigarette or vaping apparatus are likely to fall within the defined size ranges, or at least a significant proportion of them will fall within the defined size ranges. For example, 50% of the active component aerosols falling within the defined size ranges may be reasonably expected. It is preferable if a greater percentage falls within the defined size range, for example 75% or even higher. However, it may be acceptable to have a lower percentage such as down to 25% of the active component aerosols within the defined size ranges.

Flavour component aerosols may be generated in a number of ways of which some have been described above. The creation of aerosols (sometimes referred to as "atomisation") has been described in technical and scientific literature and such techniques may be applied, adapted to or modified for the flavour aerosol generators and elements the utilisation embodiments in accordance with the present invention. An overview of aerosolisation and techniques and methods for generating aerosols will now be provided. For the avoidance of doubt, references to droplet or particle are also references to aerosols may comprise a droplet such as a vapour condensate and/or a solid particle.

Figure 13:
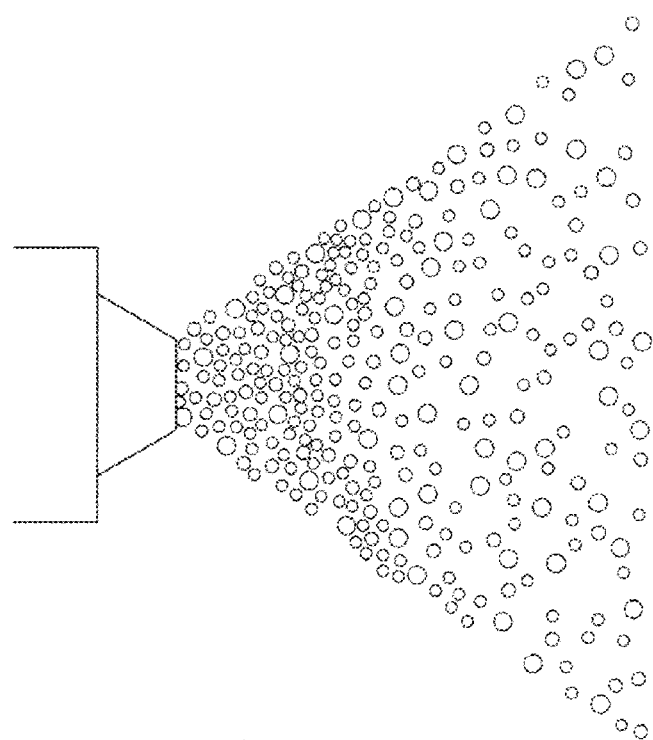
FIG. 13 is a schematic illustration of an atomiser.

Aerosols are formed initially from atomisation or from the condensing of vapour. Atomisation is the process of breaking up bulk fluids into droplets or particles. The process of breaking up the bulk fluids into a spray or aerosol that carries particles is commonly achieved using a so-called atomizer. Common examples of atomizers include shower heads, perfume sprays, and hair or deodorant sprays. FIG. 13 is a schematic illustration of a typical atomiser and the range of particle sizes produced therefrom.

An aerosol is a collection of moving particles that are the result of atomization; for most non-naturally occurring applications of atomization the aerosol moves the particles in a controlled fashion and direction. Typically, for most everyday applications the aerosol comprises a range of particle sizes depending upon various intrinsic and environmental parameters as discussed below.

A droplet or particle of fluid has a more or less spherical shape due to the surface tension of the fluid. The surface tension causes sheets or ligaments of fluid to be unstable; i.e. to break up into particles and/or atomize. As a general rule, as the temperature of the fluid increases its surface tension tends to correspondingly decrease.

A variety of properties and factors affect the size of the droplets or particles and how easily the fluid may be atomized after being ejected from an aperture; these include surface tension, viscosity, and density.

Surface Tension: surface tension tends to stabilize a fluid preventing it from separating into droplets of particles. Fluids with a higher surface tension tend to produce droplets or particles with a larger average droplet size or diameter upon atomization.

Figure 14:
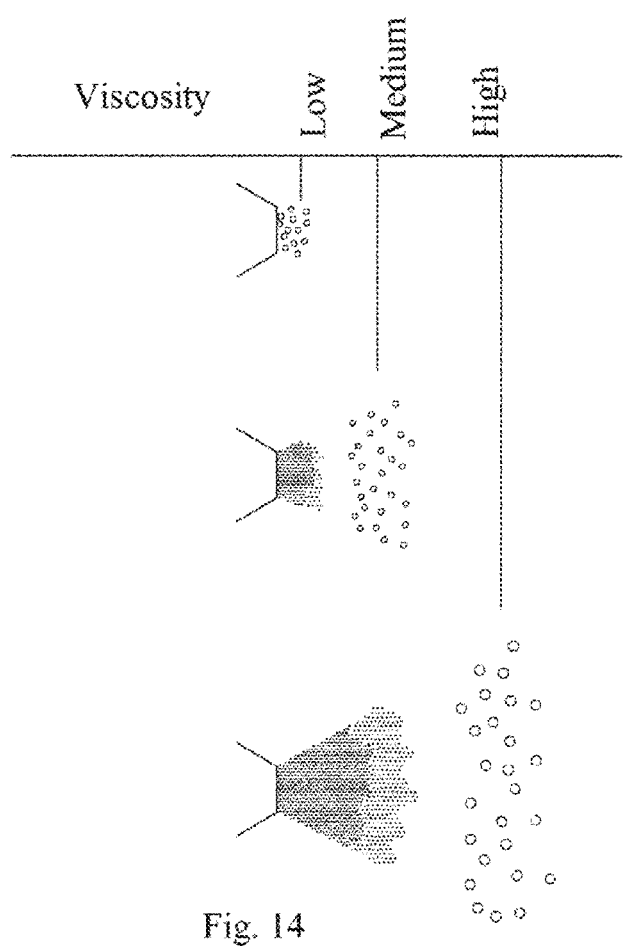
FIG. 14 is a graphical illustration of the variation of aerosol size with viscosity of precursor liquid.

Viscosity: the viscosity of a fluid has a similar effect on the size or diameter of the droplet or particle formed during atomization as surface tension. The viscosity of fluid resists agitation preventing the bulk fluid from breaking into droplets or particles. Consequently, fluids with a higher viscosity tend to produce droplets or particles with a larger average droplet size or diameter upon atomization. FIG. 14 graphically illustrates the relationship between viscosity and droplet size when atomization occurs and aerosols formed.

Density: density causes the fluid to resist acceleration. Consequently, once again fluids with a higher density tend to produce droplets or particles with a larger average droplet size or diameter upon atomization.

Atomization Processes

The process of atomisation, i.e. the process that may lead to the formation of aerosols, may take a number of different forms.

Pressure Atomization

Figure 15:
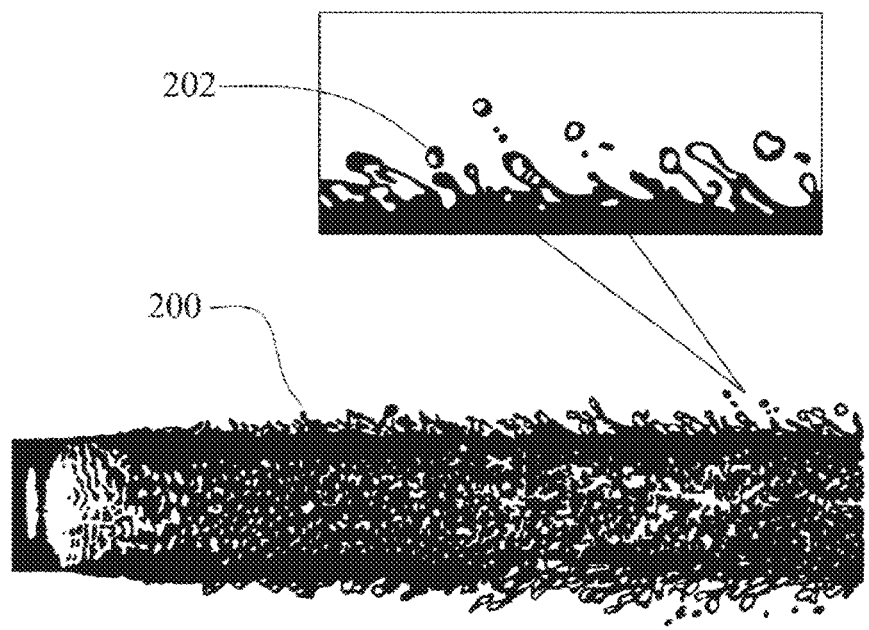
FIG. 15 is an illustration of aerosol formation from a high velocity liquid jet.

Also known as airless, air-assisted airless, hydrostatic, and hydraulic atomization, the pressure atomization process involves forcing fluid through a small nozzle or orifice at high pressure so that the fluid is ejected at high speed as a solid stream or sheet. The friction between the fluid and air disrupts the stream, causing it to break into fragments initially and ultimately into droplets. FIG. 15 schematically illustrates a high-velocity water jet 200 that breaks up into droplets 202 in an airless atomization system. In such a system a high-velocity water jet is expelled from a suitable aperture.

A number of factors affect the stream and droplet size including the diameter of the orifice, the external atmosphere (temperature and pressure), and the relative velocity of the fluid and air. As a general rule, the larger the diameter of the nozzle orifice, the larger the average droplet diameter in the spray.

The external atmosphere resists the spray and tends to break up the stream of fluid; this resistance tends to partially overcome the surface tension, viscosity and density of the fluid.

Figure 16:
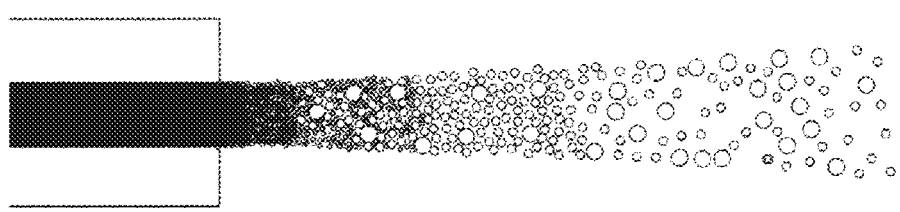
FIG. 16 is a schematic illustration of aerosol formation from a pressurised fluid exiting an aperture.

The relative velocity between the fluid and air has the greatest influence on the average diameter of the droplets in the aerosol. Since the velocity of the fluid ejected through the nozzle orifice is dependent upon pressure, as fluid pressure in the nozzle increases the average diameter of the droplets correspondingly decreases. Conversely, as fluid pressure decrease, the velocity is lower and the average diameter of the droplets increases. FIG. 16 schematically illustrates an airless atomization process in which pressurized fluid is ejected from a circular orifice into the atmosphere.

Air Atomization

Figure 17:
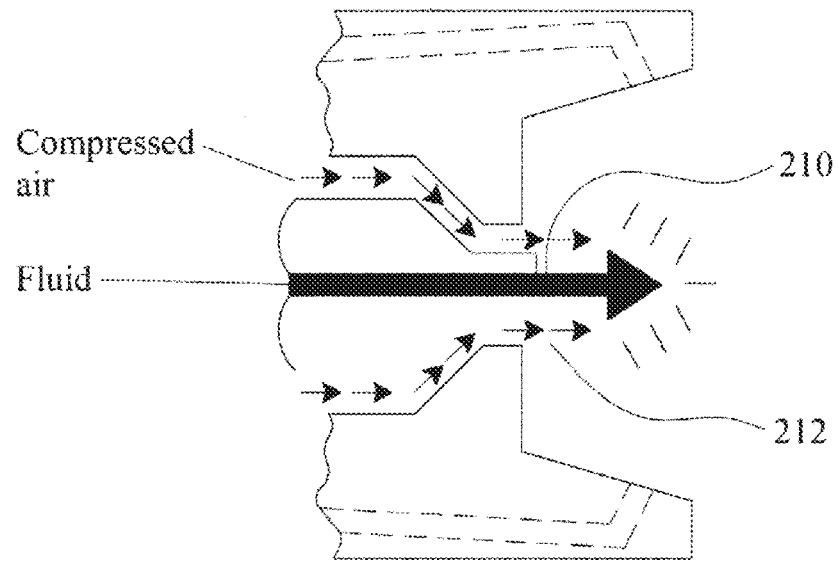
FIG. 17 is a schematic illustration of a device for air atomisation.

In air atomization, fluid is ejected from a nozzle orifice 210 at relatively low speed and low pressure and is surrounded by a high-velocity stream of air 212. Friction between the fluid and air accelerates and disrupts the fluid stream and causes atomization. As the principal energy source for atomization is air pressure, the fluid flow rate can be regulated independently of the energy source. Accordingly, air atomization has been adopted as the principal technology for atomization in medical inhalation and device technologies. FIG. 17 schematically illustrates such an arrangement with a stream of fluid passing through an orifice in which as the stream of fluid emerges, a high-speed stream of air surrounds the fluid stream.

Centrifugal Atomization

Figure 18:
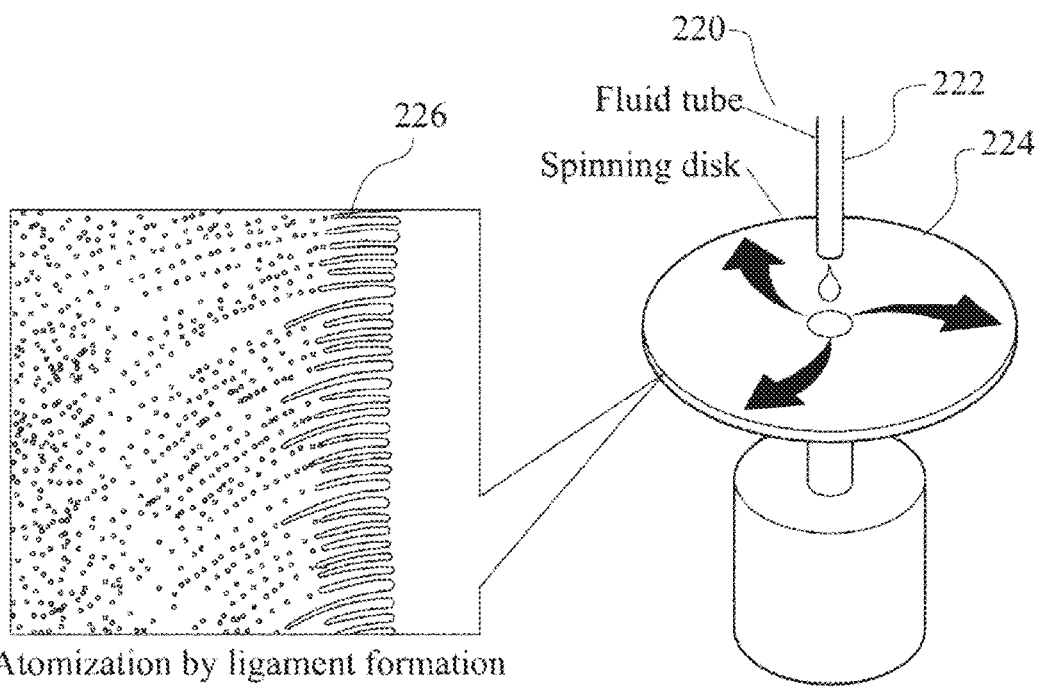
FIG. 18 is a schematic illustration of a centrifugal atomiser.
Figure 19:
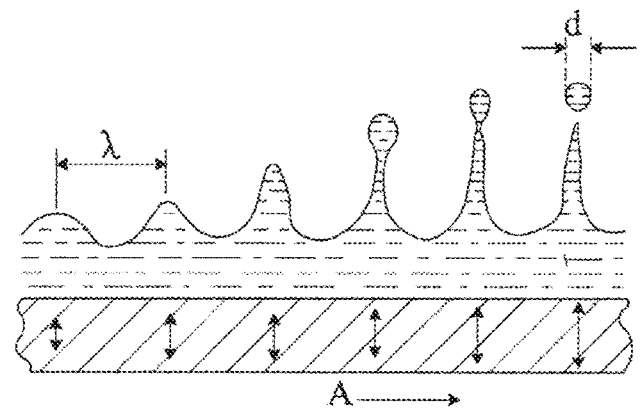
FIG. 19 is a schematic illustration of aerosol formation in an ultrasonic atomisation.
Figure 20:
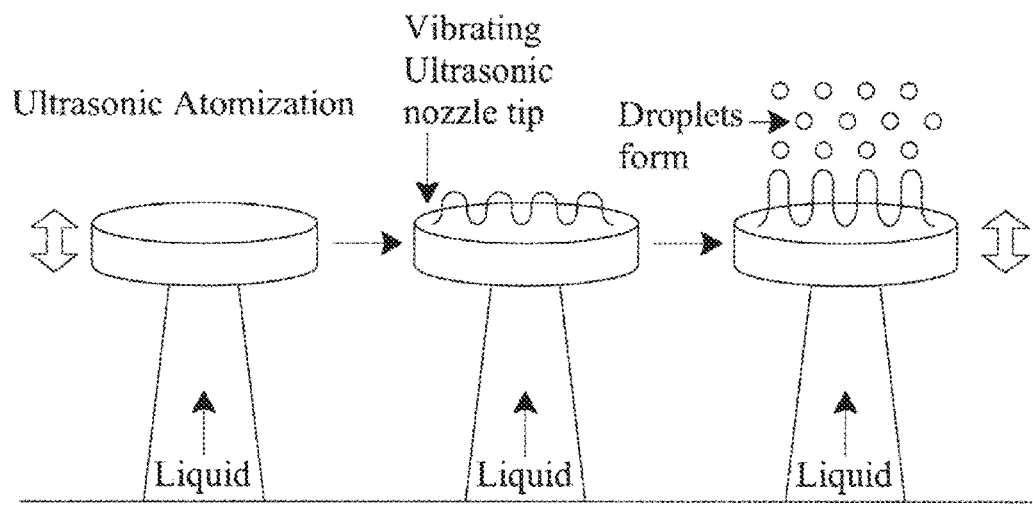
FIG. 20 is a schematic illustration of a structure for ultrasonic atomisation.

FIG. 18 schematically illustrates a centrifugal or rotary atomization system 220 (also known as rotary atomization). A nozzle 222 introduces fluid in the centre of a spinning disk 224 or cone. Centrifugal forces carry the fluid to the edge of the disk or cone. As it is ejected from the edge of the disk or cone the liquid forms ligaments 226 or sheets that break the bulk liquid into droplets or particles.

At the same rotational speed, at slow fluid flow rates droplets form closer to the edge of the disk than with higher flow rates. The fluid is ejected from the edge of the disk and moves radially away from the disk in all directions (i.e. 360°). Accordingly, where the droplets may be entrained in a directional air flow or shaping bell to cause the aerosol to travel in an axial direction.

Both the flow rate of the fluid introduced onto the spinning disk or cone, and the disk speed can be controlled independently of each another.

Ultrasonic Atomization

Ultrasonic atomization relies on an electromechanical device that vibrates at high frequency. The high-frequency oscillation causes fluid passing over or through the vibrating surface to break into droplets.

There are a number of types of ultrasonic nebulisers including ultrasonic wave atomizers and vibrating mesh atomizers.

Ultrasonic Wave Atomizers

A thin layer of liquid is deposited on the surface of a resonator (typically a resonating surface connected to a piezo-electric element) which is then mechanically vibrated at high-frequency along direction A. The vibrations cause a pattern of standing capillary waves having a standing wavelength I when the vibration amplitude exceeds a threshold value. Upon increasing the vibration amplitude above the threshold ligament break-up of the liquid occurs and droplets are expelled from the crests/peaks of the capillary waves. FIG. 19 schematically illustrates the principles of operation of an ultrasonic atomization system.

As schematically illustrated in FIG. 20, disc-shaped ceramic piezo-electric transducers or resonators convert electrical energy into mechanical energy. The transducers receive an electrical input in the form of a high-frequency signal from a power generator and convert it into vibratory motion at the same frequency. Two titanium cylinders magnify the motion and increase the vibration amplitude of the atomizing surface.

The nozzle is designed so that excitation of the piezo-electric crystal comprised in the transducer create a standing wave along the length of the nozzle. The ultrasonic energy from the crystals located in the large diameter of the nozzle body undergoes a step transition and amplification as the standing wave as it traverses the length of the nozzle.

Since the wavelength is dependent upon operating frequency, nozzle dimensions are governed by frequency. In general, high-frequency nozzles are smaller, create smaller droplets, and consequently have a smaller maximum flow capacity than nozzles that operate at lower frequencies.

The nozzle is preferably fabricated from titanium because of its good acoustical properties, high tensile strength, and excellent corrosion resistance. Liquid is introduced onto the atomizing surface through a feed tube running the length of the nozzle that absorbs some of the vibrational energy, setting up a wave motion in the liquid on the surface. For the liquid to atomize, the vibrational amplitude of the atomizing surface must be carefully controlled. Below the so called critical amplitude, the energy is insufficient to produce atomized droplets and if the amplitude is excessively high the liquid is ripped apart and 'chunks' of fluid are ejected (a condition known as "cavitation").

Since the ultrasonic atomization relies only on liquid being introduced onto the atomizing surface, the rate at which liquid is atomized depends solely on the rate at which it is delivered to the surface.

Ultrasonic wave atomizers are particularly suited to low pressure/low velocity applications and provide an aerosol spray that is highly controllable. Accordingly, since the atomization process is not reliant upon fluid pressure the volume of liquid that is atomized can be controlled by the liquid delivery system and can range from a few microliters upwards. In addition the aerosol spray can be precisely controlled and shaped by entraining the low-velocity aerosol spray in an ancillary air stream to produce a spray pattern that is as small as around 1.8 mm wide.

Furthermore, droplets produced by ultrasonic vibration have a relatively narrow average diameter distribution. Median droplet sizes range from 18-68 microns, depending upon the operating frequency of the nozzle. For example, Sono-Tek claim that their ultrasonic spray nozzles can produce a median droplet diameter of around 40 microns with 99.9% of the droplets having a diameter falling in the range 5-200 microns.

Static Mesh Atomization

Static mesh atomizers apply a force to the liquid to force it through a static mesh as shown in FIG. 21. An ultrasonic transducer is used to generate vibrations in the liquid and push the droplets through the static mesh.

Vibrating Mesh Atomization

Vibrating mesh atomisers use mesh deformation or vibration to push liquid through the mesh as schematically shown in FIG. 22. Typically, an annular piezo-electric element that is contact with the mesh is used to produce vibrations around the mesh. Holes in the mesh have a conical structure, with the largest cross-section of the cone in contact proximal to the liquid reservoir. The face of the mesh deforms towards the liquid reservoir thus pumping liquid into and loading the holes with liquid. The deformation of the face on the other side of the mesh ejects droplets through the holes.

The size of the droplet and aerosol produced is dependent on the size of the holes in the mesh and the physiochemical properties of the liquid. However, one of the drawbacks to vibrating mesh devices is the potential for the holes in the mesh to clog particularly with solutions that are too viscous to pass through the mesh.

More detail concerning the various techniques for generating aerosols via atomisation may be found in the following publications.

"Deposition of Inhaled Particles in the Lungs", Ana Fernandez Tena, Pere Casan Clara; ARCHIVOS DE BRONCONEUMOLOGIA, 2012; 48(7) 240-246.

"The mesh nebuliser: a recent technical innovation for aerosol delivery", L. Vecellio; breathe, March 2006, Volume 2, No. 3, pp 253-260.

"Ultrasonic Atomisation Technology for Precise Coatings", Sono-Tek Corporation at http://www.sono-tek.com/ultrasonic-nozzle-technology/and downloaded 23 May 2017.

"High-Frequency Ultrasonic Atomisation with Pulsed Excitation", A. Lozano, H. Amaveda, F. Barreras, X. Jorda, M. Lozano; Journal of Fluid Engineering, November 2003, Vol. 125, 941-945.

"Swirl, T-Jet and Vibrating-Mesh Atomisers", M. Eslamian, Nasser Ashgriz; ResearchGate; http://www.researchgate.net/publications/251220009, December 2011.

FIGS. 23 and 24 each show a substitute smoking system in accordance with the present invention. In FIG. 23, the components of the substitute smoking system are separated from one another. In FIG. 24, the components of the substitute smoking system are engaged with one another.

As shown in FIGS. 23 and 24, the substitute smoking system includes a substitute smoking device 300. Two types of consumable 301, 302 are also shown—a cartomiser 301 and a flavour pod 302. The cartomiser 301 is configured to engage directly with the substitute smoking device 300. The cartomiser 301 may engage with the substitute smoking device 300 via a push-fit engagement, a screw-thread engagement, or a bayonet fit, for example. A cartomiser may also be referred to as a "pod".

The flavour pod 302 is configured to engage with the cartomiser 301 and thus with the substitute smoking device 300. The flavour pod 302 may engage with the cartomiser 301 via a push-fit engagement, a screw-thread engagement, or a bayonet fit, for example. FIG. 24 illustrates the cartomiser 301 engaged with the substitute smoking device 300, and the flavour pod 302 engaged with the cartomiser 301. As will be appreciated, in the system of FIGS. 22 and 23, the cartomiser 301 and the flavour pod 302 are distinct elements. Both the cartomiser 301 and/or the flavour pod may be a consumable according to the present invention.

A "consumable" component may mean that the component is intended to be used once until exhausted, and then disposed of as waste or returned to a manufacturer for reprocessing.

Each of the substitute smoking device 300, cartomiser 301, and flavour pod 302 are generally elongate elements. Each has a longitudinal axis that is parallel with the longest axis of the respective element.

As will be appreciated from the following description, the cartomiser 301 and the flavour pod 302 may alternatively be combined into a single component that implements the functionality of the cartomiser 301 and flavour pod 302. Such a single component may also be a consumable according to the present invention.

FIGS. 25 and 26 illustrate a substitute smoking system in accordance with the present invention including a substitute smoking device 300 and a single consumable 303. The consumable 303 combines the functionality of the cartomiser 301 and the flavour pod 302. In FIG. 25, the components of the substitute smoking system are separated from one another. In FIG. 26, the components of the substitute smoking system are engaged with one another.

Each of the substitute smoking device 300 and the consumable 303 are generally elongate elements. Each has a longitudinal axis that is parallel with the longest axis of the respective element.

FIG. 27 shows a consumable 303 in accordance with the present invention that implements the functionality of a cartomiser 301 and a flavour pod 302 in accordance with the present invention.

In FIG. 27, the consumable 303 is shown engaged with a substitute smoking device 300 via a push-fit engagement. The consumable 303 is a single component (as in FIGS. 25 and 26). The consumable 303 may be considered to have two portions—a cartomiser portion 304 and the flavour pod portion 305.

The consumable 303 includes an upstream inlet 306 and a downstream outlet 307. A particular consumable may include a plurality of inlets and/or or a plurality of outlets. Between the inlet 306 and the outlet 307 there is an airflow passage 308. The outlet 307 is located at the mouthpiece end 309 of the consumable 303. A user draws (or "sucks", or "pulls") on the mouthpiece end 309 of the consumable 303. When a user draws on the mouthpiece end 309, the drop in air pressure at the outlet 307 causes an airflow into the inlet 306, along the airflow passage 308, and out from the outlet 307. The airflow flows out from the outlet 307 located at the mouthpiece end 309 and into the user's mouth.

The cartomiser portion 304 of the consumable 303 includes an e-liquid storage tank 310. The e-liquid storage tank 310 contains a supply of e-liquid ("vapour precursor material"), which corresponds to a first aerosol precursor. Extending into the e-liquid storage tank 310 is a wick 311. The wick 311 is formed from a porous wicking material (e.g. a polymer) that draws e-liquid from the e-liquid storage tank 310 into a central region of the wick 311 that is located outside the e-liquid storage tank 310.

A heater 312 is a configured to heat the central region of the wick 311. The heater 312 includes a resistive heating filament that is coiled around the central region of the wick 311. The wick 311, the heater 312 and the e-liquid storage tank 310 may correspond to an active aerosol generator (or "first aerosol generator").

When the heater 312 is activated (by passing an electric current through the heating filament) the e-liquid located in the wick 311 adjacent to the heating filament is heated and vapourised to form a vapour. The vapour may condense to form the first aerosol. The first vapour/aerosol is generated within the airflow passage 308. Accordingly, the first aerosol is entrained in an airflow along the airflow flow passage 308 to the outlet 307 and ultimately out from the mouthpiece end 309 for inhalation by the user when the user draws on the mouthpiece end 309.

So that the consumable 303 may be supplied with electrical power for activation of the heater 312, the consumable 303 includes a pair of consumable electrical contacts 313. The consumable electrical contacts 313 are configured for electrical connection to a corresponding pair of electrical supply contacts 314 in the substitute smoking device 300. The consumable electrical contacts 313 are electrically connected to the electrical supply contacts 314 when the consumable 303 is engaged with the substitute smoking device 300. The substitute smoking device 300 includes an electrical power source (not shown), for example a battery. The substitute smoking device 300 supplies electrical current to the consumable electrical contacts 313. This causes an electric current flow through the heating filament of the heater 312 and the heating filament heats up. As described, the heating of the heating filament causes vapourisation of the e-liquid in the wick 311 to form the first aerosol.

As above, the consumable 303 includes a flavour pod portion 305. The flavour pod portion 305 is configured to generate a second (flavour) aerosol for output from the outlet 307 of the mouthpiece end 309 of the consumable 303. The flavour pod portion 305 of the consumable 303 includes a porous nib 315. The porous nib 315 may correspond to a passive aerosol generator ("second aerosol generator"). The porous nib 315 is an example of a porous member.

A flavour liquid storage tank 316 is fluidly connected to the porous nib 315. The porous nature of the porous nib 315 means that flavour liquid from the flavour liquid storage tank 316 is drawn into the porous nib 315. As the flavour liquid in the porous nib 315 is depleted, further flavour liquid is drawn from the flavour liquid storage tank 316 into the porous nib 315 via a wicking action.

The porous nib 315 is located within the airflow passage 308 through the consumable 303. The porous nib 315 constricts or narrows the airflow passage 308. The airflow passage 308 may be narrowest adjacent to the porous surface 318 of the porous nib 305. The constriction may correspond to a Venturi aperture 319. The constriction of the airflow passage 308 causes a decrease in air pressure in the airflow in the vicinity of the porous surface 318 of the porous nib 315. The corresponding low pressure region causes the generation of the second (flavour) aerosol from the porous surface 318 of the porous member 315.

It will be appreciated that the flavour storage tank 316 may be omitted. The porous nib 315 may act as the store of the flavour liquid. For example, the porous nib 315 may be soaked in flavour liquid ("second aerosol precursor"). As the flavour liquid is depleted at the porous surface 318, wicking action may replace that depleted liquid from a storage region of the porous nib 315.

Figures 23, 24:
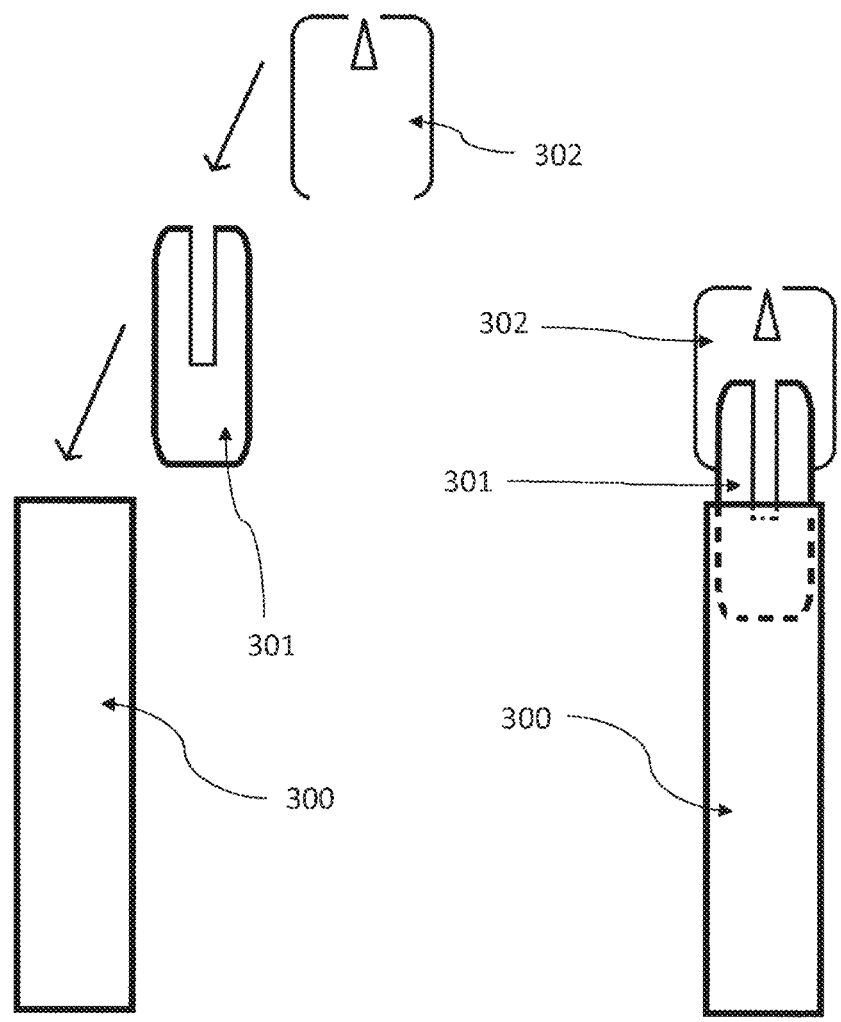
FIG. 23 is a schematic illustration of a substitute smoking system in accordance with the present invention in a separated configuration.
FIG. 24 is a schematic illustration of the substitute smoking system of FIG. 23 in a connected configuration.
Figures 25, 26:
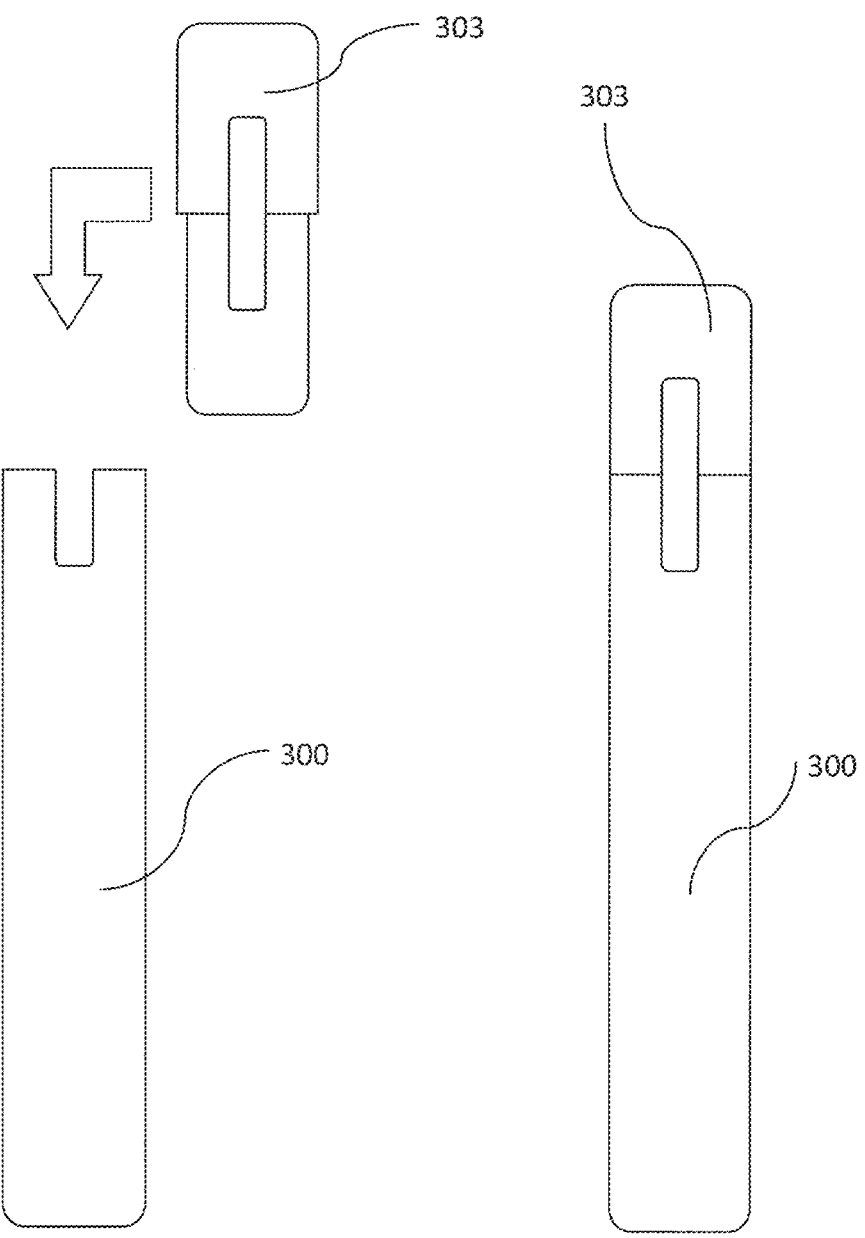
FIG. 25 is a schematic illustration of a substitute smoking system in accordance with the present invention in a separated configuration.
FIG. 26 is a schematic illustration of the substitute smoking system of FIG. 25 in a connected configuration.

The porous nib 315 is located within the airflow passage 308 of the consumable 303. In FIG. 24, an upstream portion of the porous nib 315 is seated within a nib housing 317. A downstream portion of the porous nib 315 is exposed to an airflow through the airflow passage 308. As the airflow flows across the porous surface 318 of the porous nib 315, the second (flavour) aerosol is generated from the porous nib 315. The second (flavour) aerosol is entrained into the airflow and ultimately is output from the outlet 307 of the consumable 303 and thus from the mouthpiece end 309 into the user's mouth.

The active aerosol generator (corresponding to a first aerosol generator) and the passive aerosol generator (corresponding to a second aerosol generator) may both be located within the airflow passage 308. The passive aerosol generator may be located downstream of the active aerosol generator. In use, the airflow that flows across the porous surface 318 of the porous member 315 may have the first aerosol entrained within it.

As above, the active aerosol generator corresponds to a first aerosol generator to generate a first aerosol from a first aerosol precursor (e.g. e-liquid). The first aerosol may be sized for pulmonary penetration, as described above. The description above in respect of the properties of the first aerosol is applicable to the aerosol generated by the active aerosol generator. The active aerosol generator is a powered aerosol generator. That is, the active aerosol generator generates vapour/aerosol in response to a supply of electrical power.

The passive aerosol generator corresponds to a second aerosol generator to generate a second aerosol from a second aerosol precursor (e.g. flavour liquid). The second aerosol may be sized to inhibit pulmonary penetration, as described above. The description above in respect of the properties of the second aerosol is applicable to the aerosol generated by the passive aerosol generator. The passive aerosol generator does not require a supply of electrical energy to produce the second aerosol. In a consumable including both active and passive aerosol generator, the passive aerosol generator may be configured to be electrically isolated from the electrical energy supply that supplies the active (first) aerosol generator. The passive aerosol generator is configured to generate vapour/aerosol in the absence of a supply of electrical power.

As above, the second aerosol may be transmissible within at least one of: a mammalian oral cavity and a mammalian nasal cavity, and the second aerosol may comprise an active component for activating at least one of: one or more taste receptors in said oral cavity and one or more olfactory receptors in said nasal cavity.

Figure 27:
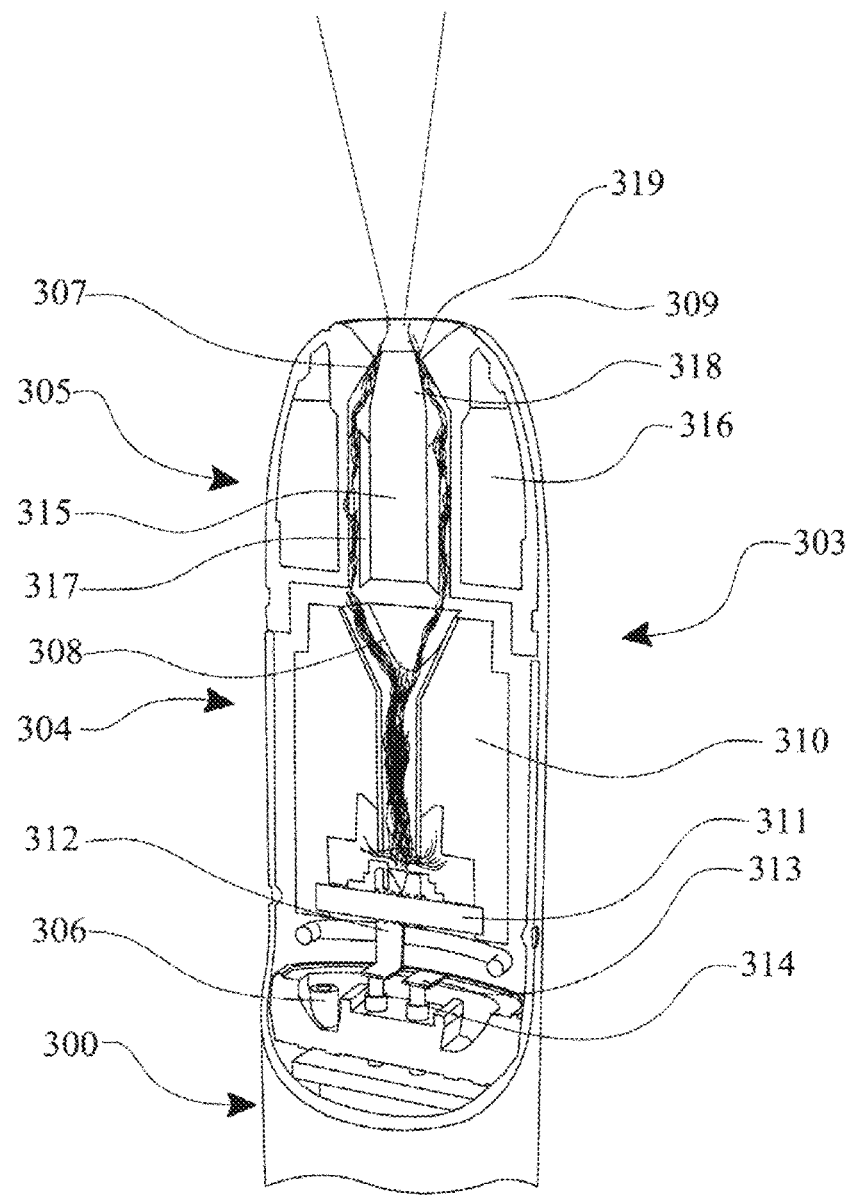
FIG. 27 is an illustration of a consumable according to the present invention.
Figure 28:
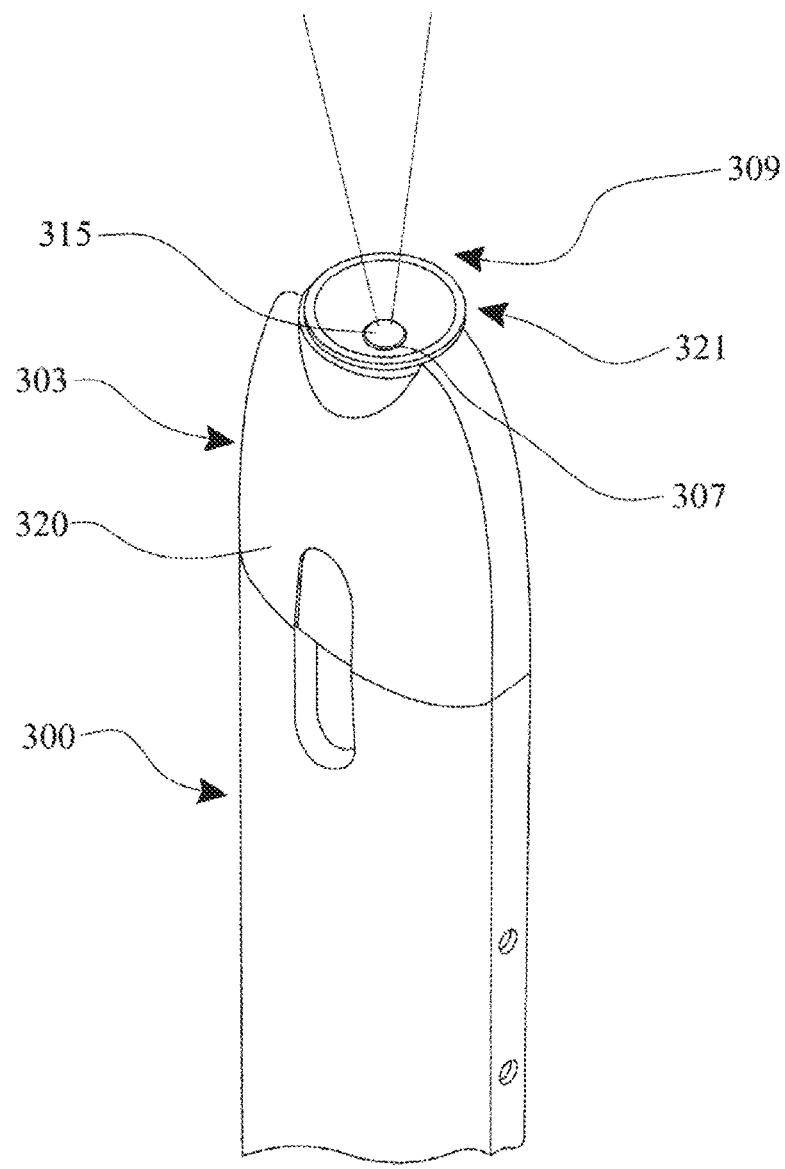
FIG. 28 is an alternative view of the consumable of FIG. 27.
Figure 29:
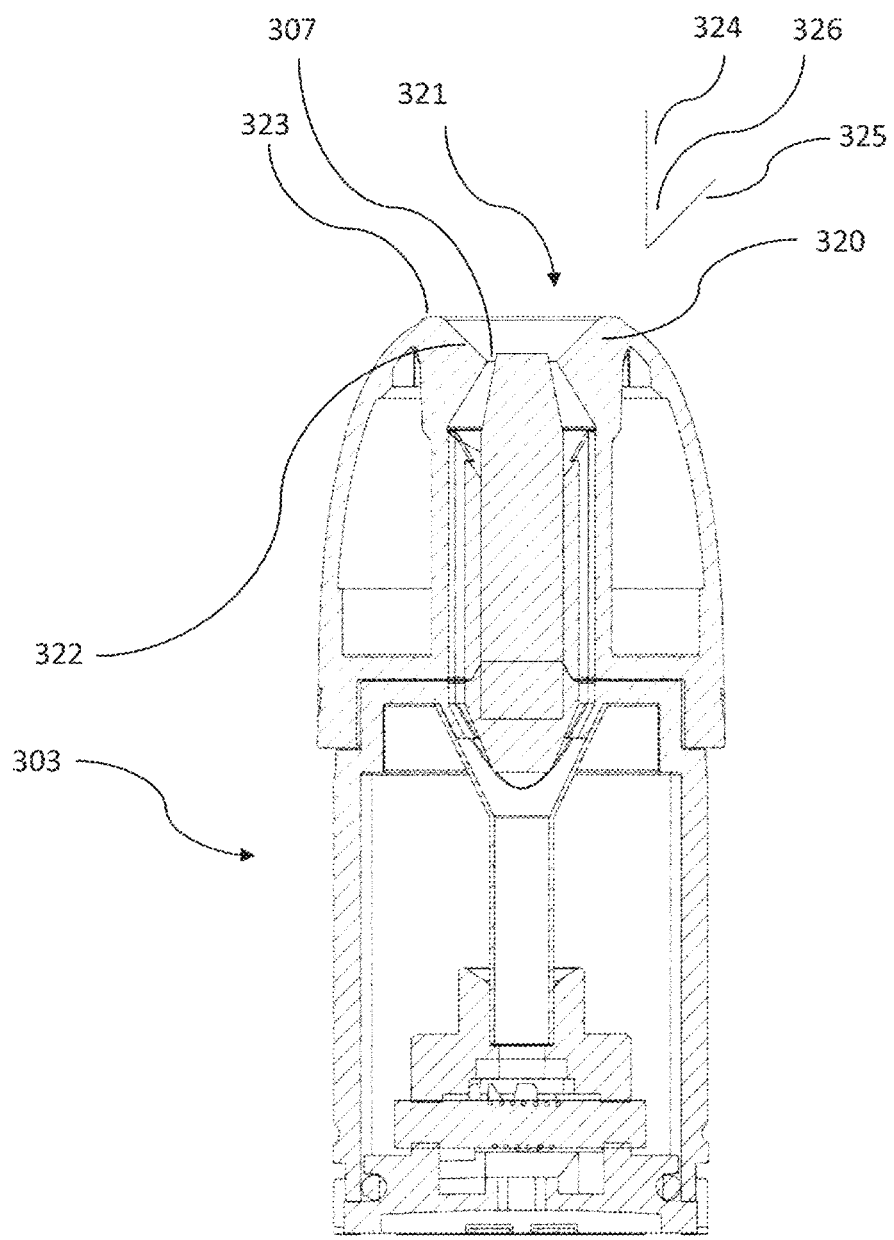
FIG. 29 is a cross section view of the consumable of FIG. 27.
Figure 30:
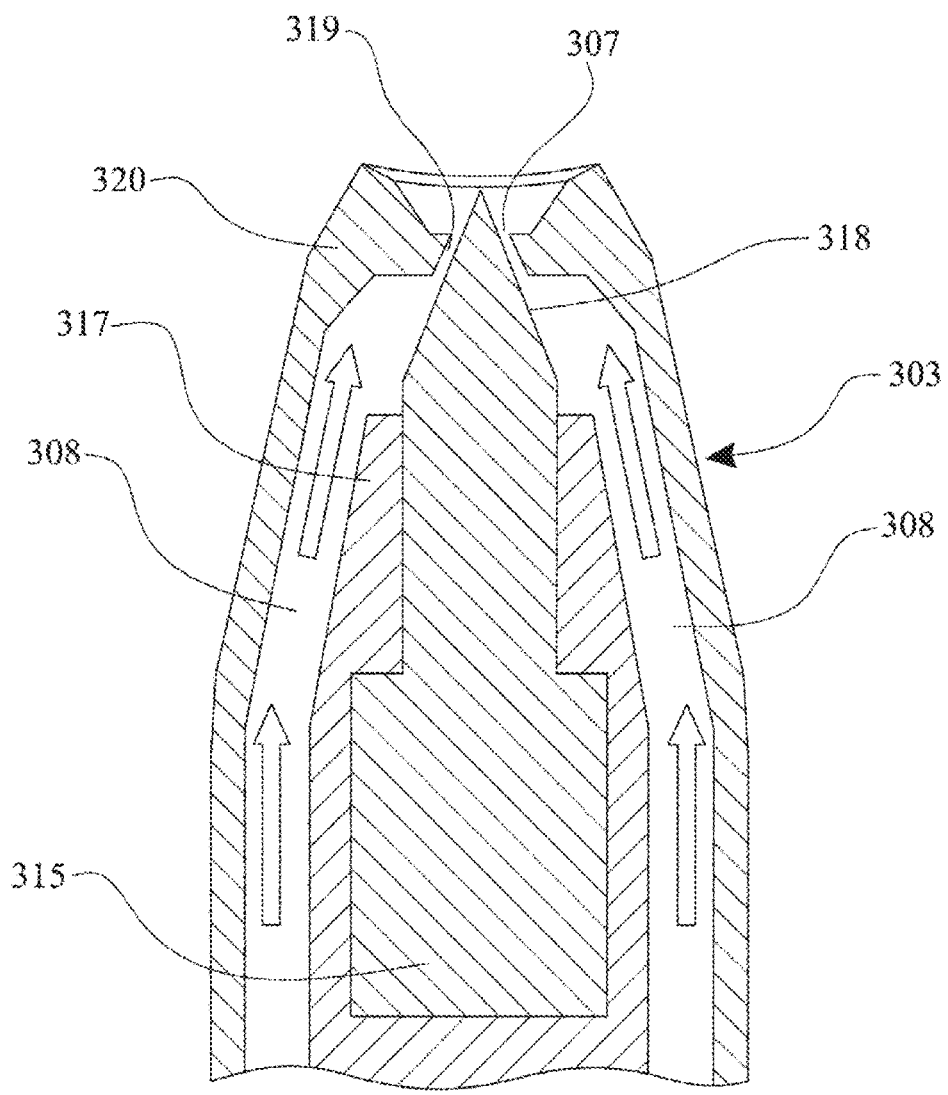
FIG. 30 is a cross section schematic of a consumable according to the present invention.
Figure 31:
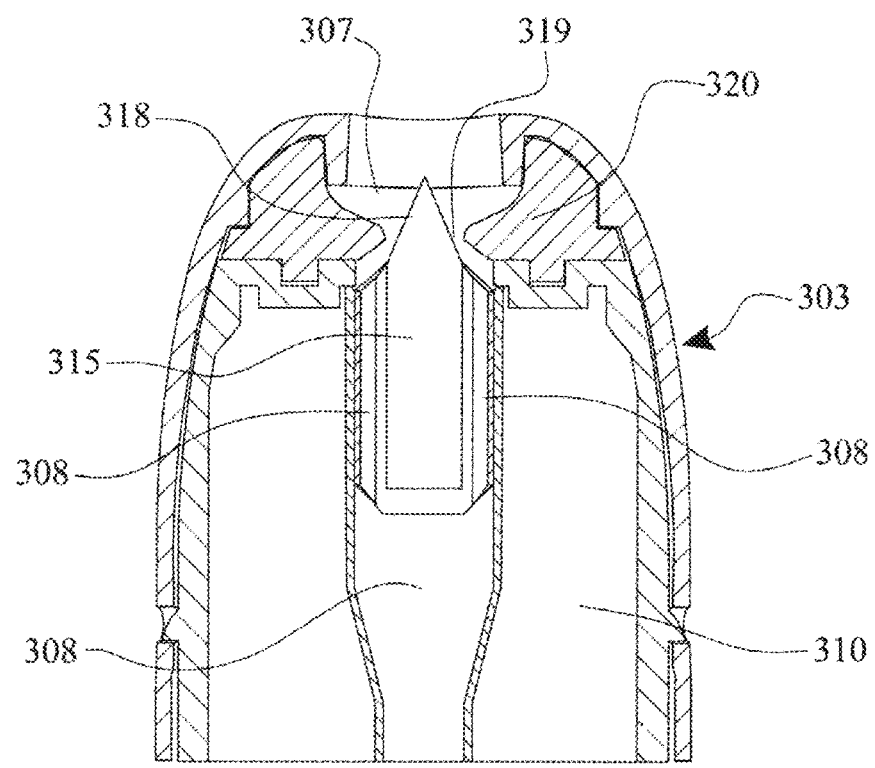
FIG. 31 is a cross section schematic of a consumable according to the present invention.

FIG. 28 shows an alternative view of the consumable 303 and substitute smoking device 300 of FIG. 27.

As shown in FIG. 28, a surface of the porous nib 315 is visible from the outside of the consumable 303 by a user during normal use of the consumable 303. More specifically, a portion of the porous nib 315 is located substantially at the outlet 307 of the consumable 303, which is in turn located at the mouthpiece end 309 of the consumable 303. In other words, an external surface of the porous nib 315 may form an external surface of the consumable 303. For example, the outlet 307 may include an aperture in the housing of the consumable 303, and the aperture is partially blocked by the porous nib 315. Having a direct line of sight to the porous nib 315 from the outlet 307 means that the second (flavour) aerosol generated at the surface of the porous nib 315 can travel from the porous nib 315 directly to the user's mouth. Consequently, the second (flavour) aerosol is more likely to exit the consumable 303 and to enter the user's mouth.

Because the second (flavour) aerosol is generated passively (i.e. without heating) the temperature of the airflow is not increased by the porous nib 315. Accordingly, it is possible for the porous nib 315 (the passive aerosol generator) can be located at or near the mouthpiece end 309. Conversely, an active aerosol generator may produce hotter vapour/aerosol which may be of an inappropriately high temperature for delivery to a user's mouth from an active generation location at or near the mouthpiece end 309.

The second (flavour) aerosol is generated as an airflow passes across a porous surface 318 of the porous nib 315. The second aerosol is generated at an aerosol generation location on the porous surface 318 of the porous nib 315. The aerosol generation location may be close to the outlet 307 of the mouthpiece end 309 of the consumable 303.

For example, the distance between the aerosol generation location and the outlet 307 may be less than 4.0 centimetres, preferably less than 3.5 centimetres, more preferably less than 3.0 centimetres, more preferably less than 2.5 centimetres, more preferably less than 2.0 centimetres, more preferably less than 1.5 centimetres, more preferably less than 1.0 centimetres, more preferably less than 0.5 centimetres.

The distance between the aerosol generation location and the outlet 307 may be greater than 3.5 centimetres, preferably greater than 3.0 centimetres, more preferably greater than 2.5 centimetres, more preferably greater than 2.0 centimetres, more preferably greater than 1.5 centimetres, more preferably greater than 1.0 centimetres, more preferably greater than 0.5 centimetres.

The distance between the aerosol generation location and the outlet 307 may be selected independently from the above values. For example, the distance between the aerosol generation location and the outlet 307 may be between 0.5 cm and 2.5 cm; or between 1.5 cm and 3.5 cm.

A distance between the aerosol generation location of the passive aerosol generator and the active aerosol generator (e.g. the location of the wick and heater) may be greater than 1.0 centimetre, preferably greater than 1.5 centimetres, more preferably greater than 2.0 centimetres, more preferably greater than 2.5 centimetres, more preferably greater than 3.0 centimetres more preferably greater than 4.0 centimetres.

The distance between the aerosol generation location of the passive aerosol generator and the active aerosol generator (e.g. the location of the wick and heater) may be less than 8.0 centimetres, preferably less than 5.0 centimetres, more preferably less than 4.0 centimetres, more preferably less than 2.0 centimetres.

The distance between the aerosol generation location of the passive aerosol generator and the active aerosol generator (e.g. the location of the wick and heater) may be selected independently from the above values. For example, the distance between the aerosol generation location of the passive aerosol generator and the active aerosol generator (e.g. the location of the wick and heater) may be between 2.0 cm and 8.0 cm; or between 1.5 cm and 4.0 cm.

As shown in FIG. 28, a housing 320 of the consumable 303 includes a nozzle 321 surrounding the exposed surface of the porous nib 315 and outlet 307. The nozzle 321 is surrounded by a peripheral wall 322. The exposed surface of the porous nib 315 is recessed within the cavity 321. One function of the nozzle 321 may be to prevent and/or reduce the possibility of inadvertent damage being caused to the porous nib 315.

FIG. 29 illustrates a cross section through the consumable 303 of FIG. 28. As described above, the housing 320 of the consumable 303 includes a nozzle 321. The nozzle 321 and the housing 320 are unitary elements in the embodiment of FIG. 29. The nozzle 321 includes an internal surrounding wall 322 and a peripheral rim 323. The nozzle 321 has a conical profile in the embodiment shown in FIG. 29. Alternatively, the nozzle 321 may have a different profile, for example a bell-shape (concave sides in cross section) or a trumpet (convex sides in cross section). The nozzle 321 is located downstream of the outlet 307. The nozzle 321 may allow control of a plume of aerosol from the outlet, for example the shape of the aerosol plume (e.g. the second aerosol).

A longitudinal axis 324 of the consumable is indicated in FIG. 29. The wall axis 325 of the internal surrounding wall 322 of the nozzle 321 in longitudinal cross section is also indicated. The opening angle 326 of the nozzle 321 is also indicated. The opening angle 326 of the nozzle 321 is the angle between the longitudinal axis 324 of the consumable 303 and the wall axis 325 of the internal surrounding wall 322 of the nozzle 321.

The opening angle 326 is greater than 0 degrees; preferably greater than 5 degrees; more preferably greater than 10 degrees; more preferably greater than 15 degrees; more preferably greater than 20 degrees; more preferably greater than 25 degrees; more preferably greater than 30 degrees; more preferably greater than 35 degrees; more preferably greater than 40 degrees; more preferably greater than 45 degrees; more preferably greater than 50 degrees; more preferably greater than 55 degrees; more preferably greater than 60 degrees; more preferably greater than 65 degrees; more preferably greater than 70 degrees; more preferably greater than 75 degrees; more preferably greater than 80 degrees; more preferably greater than 85 degrees.

The opening angle 326 is less than 90 degrees; preferably less than 85 degrees; more preferably less than 80 degrees; more preferably less than 75 degrees; more preferably less than 70 degrees; more preferably less than 65 degrees; more preferably less than 60 degrees; more preferably less than 55 degrees; more preferably less than 50 degrees; more preferably less than 45 degrees; more preferably less than 40 degrees; more preferably less than 35 degrees; more preferably less than 30 degrees; more preferably less than 25 degrees; more preferably less than 20 degrees; more preferably less than 15 degrees; more preferably less than 10 degrees; more preferably less than 5 degrees.

The opening angle 326 of the nozzle 321 may be selected independently from the above values. For example, the opening angle 326 of the nozzle 321 may be between 30 degrees and 60 degrees; or between 40 degrees and 50 degrees.

The nozzle 321 may disperse the aerosol from the outlet effectively into the user's mouth. The nozzle 321 may produce an aerosol spray with a suitable opening angle for dispersal into and within the user's mouth.

FIG. 30 illustrates a longitudinal cross section through a consumable 303 in accordance with the present invention. The consumable 303 includes a housing 320. The housing 320 may be formed from a substantially rigid plastic material, for example. The porous nib 315 is shown located within a nib housing 317. A downstream porous surface 318 of the porous nib 315 is exposed to the airflow through the airflow passage 308.

FIG. 30 is a longitudinal cross section, accordingly it will be noted that the airflow passage is annular around the porous member 315. In other words, there is an airflow passage 308 surrounding the full circumferential surface of the exposed surface 318 of the porous member 315. Having an annular airflow passage around the porous surface 318 of the porous member 315 increases the available surface area from which to generate the second (flavour) aerosol.

FIG. 30 also shows that the porous nib 315 is tapered. The tapering of the porous nib 315 is along a longitudinal axis of the consumable 303. The tapering of the porous nib 315 corresponds to a narrowing along an upstream to downstream direction. In other words a downstream portion of the porous nib 315 is narrower than an upstream portion of the porous nib 315. It will be apparent that only a tapered portion of the porous nib 315 is tapered. In the example of FIG. 30, the porous surface 318 corresponds to the outer surface of the tapered portion of the porous nib 315.

The porous nib 315 has a circular transverse cross section, however other transverse cross sectional shapes are possible. For example, oval, rectangular, square or triangular.

FIG. 30 also shows a Venturi aperture 319 formed between the porous surface 318 of the porous nib 315 and a directly adjacent opening of the housing 320. The Venturi aperture 219 is an annular aperture. The narrowest part of the airflow passage is through the Venturi aperture 320, creating the low pressure region in the airflow passage 308 adjacent to the porous surface 318 of the porous nib 315. The Venturi aperture 320 is located at the outlet 307 of the consumable 303. The downstream tip of the porous nib 315 protrudes through the outlet 307 and the Venturi aperture 320, in the example of FIG. 30.

FIG. 31 illustrates a longitudinal cross section through a consumable 303 in accordance with the present invention. The consumable 303 includes a porous nib 315 located within the airflow passage 308. Around the porous surface 318 of the porous nib 315 the airflow passage 308 is annular. The housing 320 and the porous nib 315 form a Venturi aperture 319 located adjacent to the outlet 307 of the consumable 303. The consumable 303 shown in FIG. 31 operates in the same manner as that described for the consumable 303 shown in FIGS. 29 and 30 at least in respect of the porous nib 315.

FIG. 32 illustrates a schematic cross-section through an outlet portion of a consumable 303 in accordance with the present invention. A porous nib 315 is shown extending into a Venturi aperture 319 formed by an opening in the housing 320 of the consumable 303. In this embodiment, the downstream tip of the porous member 315 is located within the outlet and within the low pressure region formed by the Venturi aperture 319. The airflow passage 308 has an annular portion, surrounding the porous surface 318 of the porous nib 315.

Figure 32:
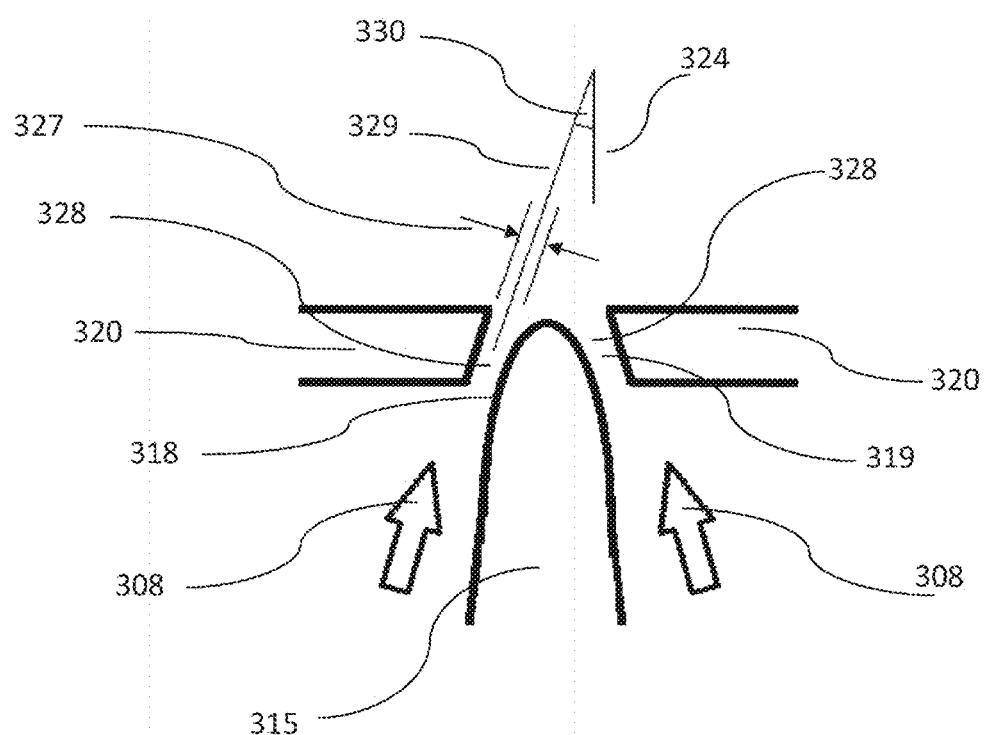
FIG. 32 is a cross section schematic of a portion of a consumable according to the present invention.

FIG. 32 illustrates the minimum distance 327 between the porous surface 318 of the porous nib 315 and the adjacent and opposing wall of the housing 320. In this embodiment, the adjacent wall is the wall of the housing 320 that defines the periphery of the Venturi aperture 319. The minimum distance 327 between the porous surface 318 of the porous nib 315 and the adjacent and opposing wall 320 may be referred to as the "contact distance", meaning the distance of closest approach.

The contact distance 327 may be less than 1000 micrometres (microns), preferably less than 900 microns, more preferably less than 800 microns, more preferably less than 700 microns, more preferably less than 600 microns, more preferably less than 500 microns, more preferably less than 400 microns, more preferably less than 300 microns, more preferably less than 250 microns, more preferably less than 200 microns, more preferably less than 150 microns, more preferably less than 100 microns, more preferably less than 50 microns, more preferably less than 30 microns, more preferably less than 15 microns.

The contact distance 327 may be greater than 5 micrometres (microns), preferably greater than 15 microns, more preferably greater than 30 microns, more preferably greater than 50 microns, more preferably greater than 100 microns, more preferably greater than 150 microns, more preferably greater than 200 microns, more preferably greater than 250 microns, more preferably greater than 300 microns, more preferably greater than 400 microns, more preferably greater than 600 microns, more preferably greater than 700 microns, more preferably greater than 800 microns, more preferably greater than 900 microns.

The contact distance 327 may be selected independently from the above values. For example, the contact distance 327 may between 30 microns and a 150 microns; or 300 microns and 900 microns.

As shown in FIG. 32, a cross section of the consumable shows the airflow passage 308 has angled (or inclined) airflow portions 328. An airflow portion axis 329 is shown for the left hand angled portion 328. The airflow portion axis 329 is not a tangible element, but merely represents a position of the angled portion 328 in cross-section. A position of a longitudinal axis 324 of the consumable 303 is also shown in FIG. 32. In longitudinal cross section, the airflow portion axis 329 forms a passage angle 330 with the longitudinal axis 324 of the consumable 303.

The passage angle 330 is less than 90 degrees, preferably less than 85 degrees, more preferably less than 80 degrees, more preferably less than 75 degrees, more preferably less than 70 degrees, more preferably less than 65 degrees, more preferably less than 60 degrees, more preferably less than 55 degrees, more preferably less than 50 degrees, more preferably less than 45 degrees, more preferably less than 40 degrees, more preferably less than 35 degrees, more preferably less than 30 degrees, more preferably less than 25 degrees, more preferably less than 20 degrees, more preferably less than 15 degrees, more preferably less than 10 degrees, more preferably less than 5 degrees.

The passage angle 330 is greater than 0 degrees, preferably greater than 5 degrees, more preferably greater than 10 degrees, more preferably greater than 15 degrees, more preferably greater than 20 degrees, more preferably greater than 25 degrees, more preferably greater than 30 degrees, more preferably greater than 35 degrees, more preferably greater than 40 degrees, more preferably greater than 45 degrees, more preferably greater than 50 degrees, more preferably greater than 55 degrees, more preferably greater than 60 degrees, more preferably greater than 65 degrees, more preferably greater than 70 degrees, more preferably greater than 75 degrees, more preferably greater than 80 degrees, more preferably greater than 85 degrees.

The passage angle 330 may be selected independently from the above values. For example, the passage angle 330 may between 15 degrees and 45 degrees; or between 55 degrees and 80 degrees.

By having an angled airflow portion 328 the length of airflow across the porous surface of 318 of the porous nib 315 can be increased per longitudinal unit length of the consumable 303. Thus, by including angled airflow portion 328, the effective porous surface area 318 of the porous nib 315 can be increased without necessarily increasing the longitudinal length of the consumable 303. This may improve the efficiency of the generation of the second (flavour) aerosol.

The length of angled airflow portion 328 along a direction of airflow along the angled airflow portion 328 may be less than 4 millimetres (mm); preferably less than 3.5 mm; more preferably less than 3.0 mm; more preferably less than 2.5 mm; more preferably less than 2.0 mm; more preferably less than 1.5 mm; more preferably less than 1.0 mm; more preferably less than 0.5 mm.

The length of angled airflow portion 328 along a direction of airflow along the angled airflow portion 328 may be greater than 0.1 millimetres (mm); preferably greater than 0.5 mm; more preferably greater than 1.0 mm; more preferably greater than 1.5 mm; more preferably greater than 2.0 mm; more preferably greater than 2.5 mm; more preferably greater than 3.0 mm; more preferably greater than 3.5 mm.

The length of angled airflow portion 328 along a direction of airflow along the angled airflow portion 328 may be selected independently from the above values. For example, the length of angled airflow portion 328 along a direction of airflow along the angled airflow portion 328 may between 1.0 mm and 2.5 mm; or between 0.1 mm and 0.5 mm.

In the embodiment shown in FIG. 32 the porous nib 315 is tapered along an upstream to downstream direction of the longitudinal axis 324 of the consumable 303. The portion of the housing 320 that opposes the porous surface 318 of the porous nib 315 is also tapered along an upstream to downstream direction of a longitudinal axis of the consumable 303. The tapering of the housing 320 and the tapering of the porous nib 315 are generally corresponding, such that the porous surface 318 of the porous nib 315 in the angled passage is generally parallel to the directly adjacent wall of the housing 320. Alternatively, the surfaces forming the walls of the angled passage 324 may not be parallel with the adjacent porous surface 318.

Alternatively, a cross section of the housing surface opposite the porous surface 318 of the porous nib 315 may also include a substantially pointed profile, the point of the profile being directed towards the porous surface 318 of the porous member 315. In other words, the contact distance is formed between the point of the housing 320 and the adjacent porous surface of the porous member 315.

FIGS. 33 to 36 illustrate example shapes for the porous nib 315 having a porous surface 318 from which the second (flavour) aerosol can be generated. In each of FIGS. 33 to 36, the general upstream to downstream airflow direction along the airflow passage 308 is shown by the arrows.

Figures 33, 34:
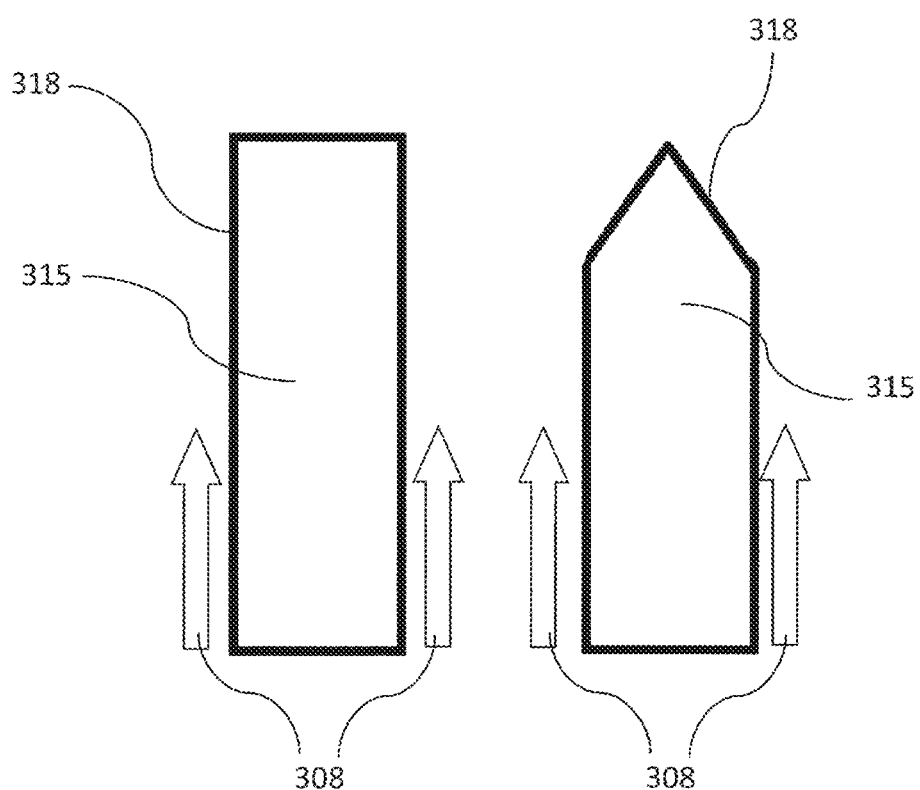
FIG. 33 is a cross section schematic of a passive aerosol generator in accordance with the present invention.
FIG. 34 is a cross section schematic of a passive aerosol generator in accordance with the present invention.

FIG. 33 shows a porous nib 315 having a cylindrical cross-sectional shape along its longitudinal length. The nib 315 is a passive aerosol generator in accordance with the present invention. The porous surface 318 from which the second (flavour) aerosol is generated is a cylindrical surface. Consequently, the cross section of the porous surface 318 is flat and generally parallel to a longitudinal axis of the consumable 303 when the porous nib 315 is located in the consumable 303. The porous nib 315 shown in FIG. 33 is not tapered.

FIG. 34 shows a porous nib 315 having a tapered downstream portion. The nib 315 is a passive aerosol generator in accordance with the present invention. The porous surface 318 from which the second (flavour) aerosol is generated is a conical surface. Consequently, the cross section of the porous surface 318 is flat and angled relative to a longitudinal axis of the consumable 303 when the porous nib 315 is located in the consumable 303. The porous nib 315 shown in FIG. 34 is tapered. The downstream tip of the porous member 315 is substantially pointed.

Figures 35, 36:
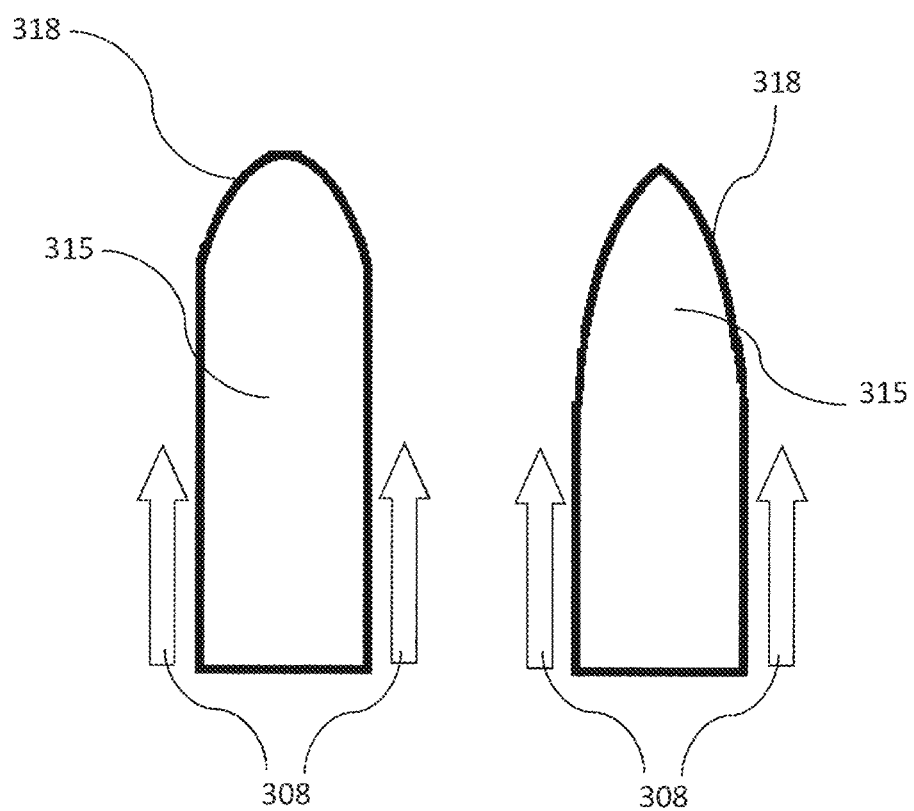
FIG. 35 is a cross section schematic of a passive aerosol generator in accordance with the present invention.
FIG. 36 is a cross section schematic of a passive aerosol generator in accordance with the present invention.

FIG. 35 shows a porous nib 315 having a tapered downstream portion. The nib 315 is a passive aerosol generator in accordance with the present invention. The porous surface 318 from which the second (flavour) aerosol is generated is a curved conical surface. Consequently, the cross section of the porous surface 318 is curved. The cross-section of the porous surface 318 of the porous nib 315 is convex. The porous nib 315 shown in FIG. 35 is tapered. The downstream tip of the porous member 315 is substantially rounded.

FIG. 36 shows a porous nib 315 having a tapered downstream portion. The nib 315 is a passive aerosol generator in accordance with the present invention. The porous surface 318 from which the second (flavour) aerosol is generated is a curved conical surface. Consequently, the cross section of the porous surface 318 is curved. The cross-section of the porous surface 318 of the porous nib 315 is convex. The porous nib 315 shown in FIG. 36 is tapered. The downstream tip of the porous member 315 is substantially pointed.

Figure 37:
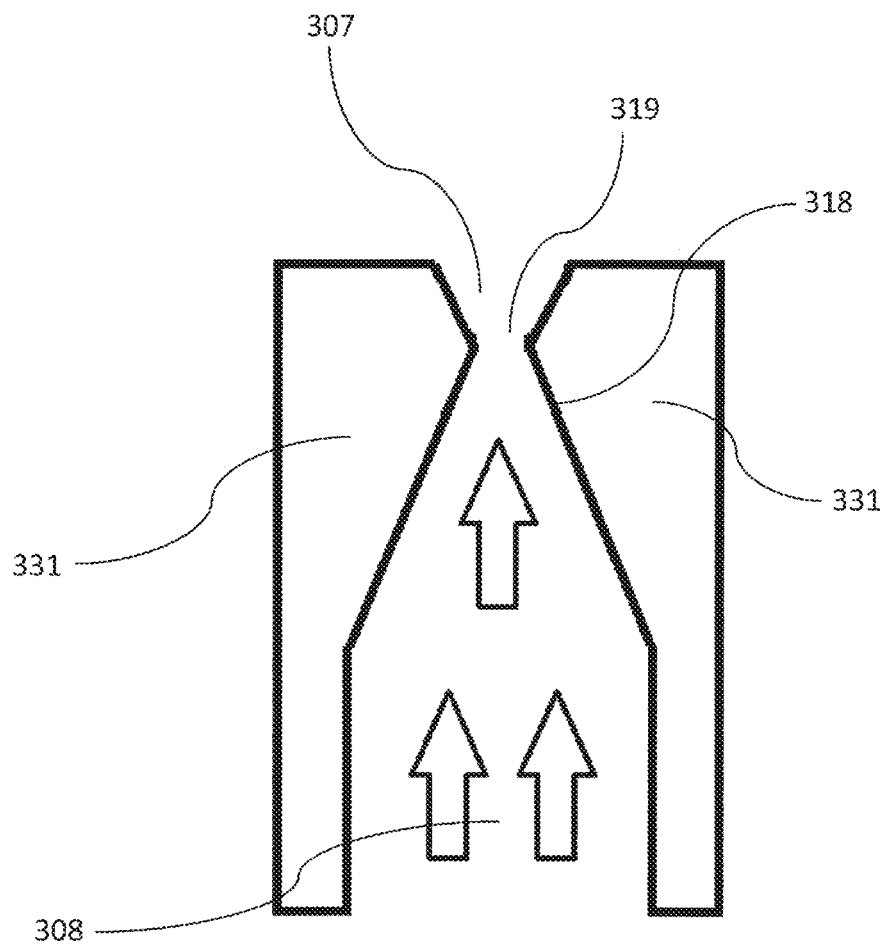
FIG. 37 is a cross section schematic of a passive aerosol generator in accordance with the present invention.

FIG. 37 shows is a cross section view through an alternative passive aerosol generator in accordance with the present invention including a porous surround 328. The porous surround 328 is similar to the porous nib 315, however the porous surround 328 surrounds at least a portion of the airflow passage 308. The airflow along the airflow passage 308 is signified by the arrows in FIG. 37. The porous surround 328 narrows along a longitudinal axis of the consumable in which it is located, constricting the airflow passage 308. A Venturi aperture 319 is located substantially at the outlet 307 of a consumable 303 that includes the porous surround 328. The porous surround 328 is configured to generate a second (flavour) aerosol at a porous surface 318 of the porous surround 328. The porous surround 328 in a consumable with a porous nib 315. The porous surround 328 may be an outer porous member and the porous nib 315 may be an inner porous member.

The techniques, methods and processes for atomising liquids to generate aerosols described above may be adapted or modified for use in one or more embodiments in accordance with the present invention.

In view of the foregoing description it will be evident to a person skilled in the art that various modifications may be made within the scope of the invention. For example, the helical spring of FIG. 4 may be a leaf spring or other resiliently deformable component such as a rubber bung.

The terms "fluid", "fluid flow", "air" and "airflow" refer to any suitable fluid composition, including but not limited to a gas or a gas mixed with an atomized, volatilized, nebulized, discharged, or otherwise gaseous phase or aerosol form of an active component.

The term "active component" includes "physiologically active" or "biologically active" and to comprise any single chemical species or combination of chemical species having desirable properties for enhancing an inhaled aerosol that is suitable for adsorption upon or absorption into media suitable for use in the present invention. Furthermore, a functional component in non-liquid form, which may for example be crystalline, powdered or otherwise solid, may be substituted for a functional component without departing from the scope of the invention.

As used herein any reference to "one embodiment" or "an embodiment" means that a particular element, feature, structure, or characteristic described in connection with the embodiment is included in at least one embodiment. The appearances of the phrase "in one embodiment" or the phrase "in an embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

We claim:

1. An aerosol delivery device comprising:
 a first aerosol generator to generate a first aerosol from a first aerosol precursor and to introduce the first aerosol into a first fluid flow pathway, wherein the first aerosol is sized for pulmonary penetration;
 a second aerosol generator to generate a second aerosol from a second aerosol precursor and to introduce the second aerosol into a second fluid flow pathway, wherein the second aerosol is sized to inhibit pulmonary penetration;

wherein the second aerosol is transmissible within at least one of: a mammalian oral cavity and a mammalian nasal cavity, and the second aerosol comprising an active component for activating at least one of: one or more taste receptors in the oral cavity and one or more olfactory receptors in the nasal cavity, and;

wherein the second aerosol generator comprises a Venturi aperture to dispense and aerosolize the second aerosol precursor in the second aerosol generator, wherein the second aerosol precursor is a liquid;

wherein the second aerosol generator comprises a porous member for containing the second aerosol precursor.

2. The aerosol delivery device according to claim 1, wherein the Venturi aperture is located proximate to an outlet at a mouthpiece outlet of the aerosol delivery device.

3. The aerosol delivery device according to claim 1, wherein the Venturi aperture is located substantially at a mouthpiece outlet of the device.

4. The aerosol delivery device according to claim 1, wherein the second aerosol is at least one of:
sized to inhibit penetration to the trachea;
sized to inhibit penetration to the larynx;
sized to inhibit penetration to the laryngopharynx; and
sized to inhibit penetration to the oropharynx.

5. The aerosol delivery device according to claim 1, wherein the second aerosol has a mass median aerodynamic diameter that is greater than or equal to 15 microns, greater than 30 microns, greater than 50 microns, greater than 60 microns, or greater than 70 microns.

6. The aerosol delivery device according to claim 1, wherein the second aerosol has a maximum mass median aerodynamic diameter that is less than 300 microns, less than 200 microns, or less than 100 microns.

7. The aerosol delivery device according to claim 1, wherein the first aerosol precursor comprises components such that the first aerosol comprises a pulmonary deliverable active component.

8. The aerosol delivery device according to claim 1, wherein the first aerosol has a mass median aerodynamic diameter less than or equal to 10 microns, less than 8 microns, less than 5 microns, or less than 1 micron.

9. The aerosol delivery device according to claim 1, wherein the first aerosol generator is configured to heat the first aerosol precursor.

10. The aerosol delivery device according to claim 1, wherein the first aerosol generator is configured to agitate the first aerosol precursor.

11. The aerosol delivery device according to claim 1, wherein the porous member includes a porous wicking material.

12. The aerosol delivery device according to claim 11, wherein a portion of the porous member is located in a low pressure region, wherein in use, the Venturi aperture forms the low pressure region.

13. The aerosol delivery device according to claim 1, wherein a portion of the porous member is located in a low pressure region, wherein in use, the Venturi aperture forms the low pressure region.

14. The aerosol delivery device according to claim 13, wherein, in use, the second aerosol is generated from a porous surface of the porous member into an airflow through the Venturi aperture.

15. The aerosol delivery device according to claim 14, wherein the porous surface is located in the low pressure region.

16. The aerosol delivery device according to claim 1, wherein the first fluid flow pathway further receives the first aerosols from a first aerosol inlet of the device.

17. The aerosol delivery device according to claim 16, wherein the first aerosol inlet is configured to inject the first aerosol into the first fluid flow pathway.

18. The aerosol delivery device according to claim 1, wherein the second fluid flow pathway further receives the second aerosol from a second aerosol inlet of the device.

19. The aerosol delivery device according to claim 18, wherein the second aerosol inlet is configured to inject the second aerosols into the second fluid flow pathway.

20. An aerosol delivery device comprising:
a first aerosol generator configured to generate a first aerosol from a first aerosol precursor and to introduce the first aerosol into a first flow pathway, wherein the first aerosol has a mass median aerodynamic diameter less than or equal to 10 microns;
a second aerosol generator including a venturi aperture and configured to generate a second aerosol from a liquid second aerosol precursor and to introduce the second aerosol into a second flow pathway, wherein the second aerosol has a mass median aerodynamic diameter greater than or equal to 15 microns; and
the second aerosol comprising an active component for activating at least one taste receptor in the oral cavity and/or at least one olfactory receptor in the nasal cavity;
wherein the second aerosol generator comprises a porous member for containing the liquid second aerosol precursor.

* * * * *